(12) United States Patent
McCullen et al.

(10) Patent No.: US 11,452,606 B2
(45) Date of Patent: Sep. 27, 2022

(54) COMPOSITE JOINT IMPLANT

(71) Applicant: Orthonika Limited, Oxford (GB)

(72) Inventors: Seth McCullen, Greenville, SC (US);
Mario Alberto Accardi, London (GB);
Maria Kristina Agius, London (GB);
Andrew Arthur Amis, London (GB)

( * ) Notice: Subject to any disclaimer, the term of this patent is extended or adjusted under 35 U.S.C. 154(b) by 0 days.

(21) Appl. No.: 16/609,834

(22) PCT Filed: May 2, 2018

(86) PCT No.: PCT/US2018/030567
§ 371 (c)(1),
(2) Date: Oct. 31, 2019

(87) PCT Pub. No.: WO2018/204440
PCT Pub. Date: Nov. 8, 2018

(65) Prior Publication Data
US 2020/0060834 A1 Feb. 27, 2020

Related U.S. Application Data

(60) Provisional application No. 62/500,006, filed on May 2, 2017.

(51) Int. Cl.
*A61F 2/38* (2006.01)
*A61B 17/56* (2006.01)
*A61F 2/30* (2006.01)

(52) U.S. Cl.
CPC ........ *A61F 2/3872* (2013.01); *A61F 2/30965* (2013.01); *A61B 17/562* (2013.01);
(Continued)

(58) Field of Classification Search
CPC ......... A61F 2/3872; A61F 2002/30754; A61B 17/562
See application file for complete search history.

(56) References Cited

U.S. PATENT DOCUMENTS

| 3,867,728 A | 2/1975 | Stubstad et al. |
|---|---|---|
| 4,195,368 A | 4/1980 | Patrichi |

(Continued)

FOREIGN PATENT DOCUMENTS

| EP | 0 372 811 A1 | 6/1990 |
|---|---|---|
| EP | 3 269 335 A1 | 1/2018 |

(Continued)

OTHER PUBLICATIONS

Extended European Search Report for European Patent Application No. 15847098.9, dated May 16, 2018 (7 pages).

(Continued)

*Primary Examiner* — Javier G Blanco
(74) *Attorney, Agent, or Firm* — Thrive IP®; Jeremy M. Stipkala

(57) ABSTRACT

A composite joint implant device replaces or repairs damaged meniscus tissue in an animal or human. In one embodiment, a composite joint implant comprises a polymeric body which is reinforced with a pre-formed engineered ligature mechanism. The ligature reinforces the polymeric body around the circumference and is used for attaching the device within an animal or human body. The ligature mechanism internally supports the transmission of vertical loads into tensile stresses. The ligature mechanism can be coated with a compatible material to promote integration with the polymeric body and coated with an encapsulation material.

12 Claims, 19 Drawing Sheets

(52) U.S. Cl.
CPC ............... *A61F 2002/30462* (2013.01); *A61F 2002/30576* (2013.01); *A61F 2002/30754* (2013.01); *A61F 2310/00005* (2013.01)

(56) References Cited

U.S. PATENT DOCUMENTS

| | | | |
|---|---|---|---|
| 4,344,193 | A | 8/1982 | Kenny |
| 4,502,161 | A | 3/1985 | Wall |
| 4,668,233 | A | 5/1987 | Seedhom et al. |
| 4,919,667 | A * | 4/1990 | Richmond ............ A61F 2/3872 623/14.12 |
| 5,116,357 | A | 5/1992 | Eberbach |
| 5,254,133 | A | 10/1993 | Seid |
| 6,093,205 | A | 7/2000 | Mcleod et al. |
| 6,113,623 | A | 9/2000 | Sgro |
| 6,113,640 | A | 9/2000 | Tormala et al. |
| 6,645,211 | B2 | 11/2003 | Magana |
| 6,679,914 | B1 | 1/2004 | Gabbay |
| 6,730,252 | B1 | 5/2004 | Teoh et al. |
| 6,736,854 | B2 | 5/2004 | Vadurro et al. |
| 6,746,485 | B1 | 6/2004 | Zucherman et al. |
| 6,755,867 | B2 | 6/2004 | Rousseau |
| 6,783,546 | B2 | 8/2004 | Zucherman et al. |
| 7,153,325 | B2 | 12/2006 | Kim et al. |
| 7,163,563 | B2 | 1/2007 | Schwartz et al. |
| 7,192,604 | B2 | 3/2007 | Brown et al. |
| 7,297,161 | B2 | 11/2007 | Fell |
| 7,341,602 | B2 | 3/2008 | Fell |
| 7,429,270 | B2 | 9/2008 | Baumgartner |
| 7,476,250 | B1 | 1/2009 | Mansmann |
| 7,572,291 | B2 | 8/2009 | Gil et al. |
| 7,758,643 | B2 | 7/2010 | Stone et al. |
| 7,871,440 | B2 | 1/2011 | Schwartz et al. |
| 7,905,922 | B2 | 3/2011 | Bergeron |
| 7,976,578 | B2 | 7/2011 | Marvel |
| 8,092,529 | B2 | 1/2012 | Malaviya |
| 8,114,156 | B2 | 2/2012 | Hatch |
| 8,282,681 | B2 | 10/2012 | Mcleod et al. |
| 8,287,594 | B2 | 10/2012 | Cragg |
| 8,292,954 | B2 | 10/2012 | Robinson |
| 8,298,290 | B2 | 10/2012 | Pelissier et al. |
| 8,357,203 | B2 | 1/2013 | White |
| 8,361,147 | B2 | 1/2013 | Shterling |
| 8,403,985 | B2 | 3/2013 | Hodorek |
| 8,623,085 | B2 | 1/2014 | Gatt |
| 8,690,919 | B2 | 4/2014 | Lange et al. |
| 8,771,353 | B2 | 7/2014 | Gedet |
| 8,858,632 | B2 | 10/2014 | Mansmann et al. |
| 8,968,419 | B2 | 3/2015 | Calvez et al. |
| 8,986,380 | B2 | 3/2015 | Kaplan et al. |
| 9,005,308 | B2 | 4/2015 | Stopek et al. |
| 9,044,278 | B2 | 6/2015 | Tanaka |
| 9,119,698 | B2 | 9/2015 | Bellon Caneiro et al. |
| 9,211,362 | B2 | 12/2015 | Hwang et al. |
| 9,314,339 | B2 | 4/2016 | Mansmann |
| 9,498,335 | B2 | 11/2016 | McCullen |
| 9,993,346 | B2 | 6/2018 | McCullen |
| 10,022,230 | B2 | 7/2018 | Amis |
| 10,034,755 | B2 | 7/2018 | McCullen et al. |
| 10,449,053 | B2 | 10/2019 | McCullen |
| 10,543,092 | B1 | 1/2020 | Huang et al. |
| 10,743,998 | B2 | 8/2020 | McCullen |
| 10,765,521 | B2 | 9/2020 | van Donkelaar et al. |
| 2002/0022884 | A1 * | 2/2002 | Mansmann ......... A61F 2/30965 623/14.12 |
| 2002/0173855 | A1 | 11/2002 | Mansmann |
| 2003/0012805 | A1 | 1/2003 | Chen et al. |
| 2003/0036797 | A1 | 2/2003 | Malaviya et al. |
| 2003/0114552 | A1 | 6/2003 | Schacht |
| 2003/0135209 | A1 | 7/2003 | Seedhom et al. |
| 2004/0059416 | A1 | 3/2004 | Murray et al. |
| 2004/0133275 | A1 | 7/2004 | Mansmann |
| 2004/0143344 | A1 | 7/2004 | Malaviya et al. |
| 2004/0266000 | A1 | 12/2004 | Offermann et al. |
| 2004/0267362 | A1 | 12/2004 | Hwang et al. |
| 2005/0027364 | A1 | 2/2005 | Kim et al. |
| 2006/0052872 | A1 | 3/2006 | Studer et al. |
| 2006/0085080 | A1 | 4/2006 | Bechgaard et al. |
| 2006/0241756 | A1 | 10/2006 | Fritz et al. |
| 2007/0073394 | A1 | 3/2007 | Seedhom et al. |
| 2007/0100450 | A1 | 5/2007 | Hodorek |
| 2007/0150063 | A1 | 6/2007 | Ruberte et al. |
| 2007/0179607 | A1 | 8/2007 | Hodorek et al. |
| 2007/0239277 | A1 | 10/2007 | Beger et al. |
| 2007/0244484 | A1 | 10/2007 | Luginbuehl |
| 2008/0086210 | A1 * | 4/2008 | Fox ......................... A61L 27/18 623/14.12 |
| 2008/0113572 | A1 | 5/2008 | Ragaru et al. |
| 2008/0154370 | A1 | 6/2008 | Mathies |
| 2008/0183292 | A1 | 7/2008 | Trieu |
| 2008/0255665 | A1 | 10/2008 | Weissberg |
| 2009/0087469 | A1 | 4/2009 | Zhang et al. |
| 2009/0132047 | A1 | 5/2009 | Mansmann et al. |
| 2009/0164014 | A1 | 6/2009 | Liljensten et al. |
| 2009/0276057 | A1 | 11/2009 | Trabucco et al. |
| 2010/0151114 | A1 | 6/2010 | Parrott |
| 2010/0222882 | A1 | 9/2010 | Badylak et al. |
| 2010/0331979 | A1 | 12/2010 | McDade et al. |
| 2011/0066243 | A1 | 3/2011 | Rivin et al. |
| 2011/0093073 | A1 | 4/2011 | Gatt et al. |
| 2011/0166494 | A1 | 7/2011 | Calvez et al. |
| 2011/0282451 | A1 | 11/2011 | Sporring |
| 2012/0045651 | A1 | 2/2012 | Myung et al. |
| 2012/0232656 | A1 | 9/2012 | Gedet et al. |
| 2012/0330093 | A1 | 12/2012 | Odermatt et al. |
| 2013/0030528 | A1 | 1/2013 | Chen et al. |
| 2013/0079877 | A1 | 3/2013 | Buma et al. |
| 2013/0138211 | A1 | 5/2013 | Myung et al. |
| 2013/0172999 | A1 | 7/2013 | Kaplan et al. |
| 2013/0190873 | A1 | 7/2013 | Mansmann |
| 2013/0204393 | A1 | 8/2013 | Samaniego |
| 2013/0268074 | A1 | 10/2013 | Vowles |
| 2013/0312897 | A1 | 11/2013 | Vowles |
| 2014/0031933 | A1 | 1/2014 | Gatt et al. |
| 2014/0114426 | A1 | 4/2014 | Forsell |
| 2014/0222149 | A1 * | 8/2014 | Amis .................. A61F 2/30756 623/14.12 |
| 2014/0277451 | A1 * | 9/2014 | Ganz .................. A61B 17/562 623/14.12 |
| 2014/0277569 | A1 | 9/2014 | Lange |
| 2014/0309739 | A1 | 10/2014 | Badylak et al. |
| 2015/0238318 | A1 | 8/2015 | McCullen |
| 2016/0228604 | A1 | 8/2016 | Mann et al. |
| 2016/0256285 | A1 * | 9/2016 | Jansen .................. A61F 2/3872 |
| 2017/0007741 | A1 | 1/2017 | D'Lima et al. |
| 2017/0065422 | A1 | 3/2017 | McCullen |
| 2017/0224498 | A1 | 8/2017 | McCullen |
| 2017/0252174 | A1 | 9/2017 | Fox |
| 2019/0076260 | A1 | 3/2019 | McCullen |
| 2019/0231534 | A1 | 8/2019 | van Donkelaar et al. |
| 2020/0000599 | A1 | 1/2020 | McCullen |
| 2020/0069434 | A1 | 3/2020 | Mimnaugh et al. |
| 2020/0163752 | A1 | 5/2020 | Salas et al. |
| 2021/0059828 | A1 | 3/2021 | McCullen |
| 2021/0298908 | A1 | 9/2021 | Holmes et al. |

FOREIGN PATENT DOCUMENTS

| | | |
|---|---|---|
| WO | 2012-159018 A1 | 11/2012 |
| WO | 2012168715 A1 | 12/2012 |
| WO | 2014055480 A1 | 4/2014 |
| WO | 2016/054463 A1 | 4/2016 |
| WO | 2016-054463 A1 | 4/2016 |

OTHER PUBLICATIONS

Written Opinion for PCT/US2013/062809, dated Jan. 10, 2014 (16 pages).
International Search Report for PCT/US2013/062809, dated Jan. 10, 2014 (4 pages).
Communication and European Search Report, for European Patent Application No. EP 13844365.0, dated May 2, 2016 (8 pages).

(56) References Cited

OTHER PUBLICATIONS

U. Klinge et al., "Modified Mesh for Hernia Repair that is Adapted to the Physiology of the Abdominal Wall," Eur. J. Surg. 164 (1998) 951-960.

T. Forstemann et al., "Forces and deformations of the abdominal wall—A mechanical and geometrical approach to the linea alba," J. Biomechanics 44 (2011) 600-606.

K. Junge et al., "Elasticity of the anterior abdominal wall and impact for reparation of incisional hernias using mesh implants," Hernia 5 (2001) 113-118.

W. S. Cobb et al., "Normal Intraabdominal Pressure in Healthy Adults," J. Surg. Res., 129 (2005) 231-235.

M. Smietanski et al., "Biomechanics of the front abdominal wall as a potential factor leading to recurrence with laparoscopic ventral hernia repair," Surg. Endosc. (Published online Dec. 15, 2011).

A. K. Williamson et al., "Compressive properties and function-composition relationships of developing bovine articular cartilage," J. Orthopaedic Res. 19 (2001) 1113-1121.

A. K. Williamson et al., "Tensile mechanical properties of bovine articular cartilage: variations with growth and relationships to collagen network components," J. Orthopaedic Res., 21 (2003) 872-880.

P. P. Pott et al., "Mechanical Properties of Mesh Materials Used for Hernia Repair and Soft Tissue Augmentation," PLOS One vol. 7, Issue 10 (2012) e46978.

International Search Report and Written Opinion for PCT/US2015/053630, dated Jan. 11, 2016 (12 pages).

Extended European Search Report for EP Pat. App. No. 19188408.9 dated Jan. 20, 2020 (9 pages).

European Search Report for EP Pat. App. No. 17 18 5178, dated Oct. 26, 2017 (2 pages).

Extended European Search Report for European Application No. 18794663.7, dated Jan. 11, 2021 (7 pages).

International Search Report for PCT/US2018/030567 dated Sep. 7, 2018 (4 pages).

Written Opinion of the International Searching Authority for PCT/US2018/030567 dated Sep. 7, 2018 (12 pages).

\* cited by examiner

COMPOSITE JOINT IMPLANT

CROSS-REFERENCE TO RELATED APPLICATIONS

The present application is the U.S. National Phase application under 35 U.S.C. § 371 of PCT Application No. PCT/US2018/030567, entitled, "COMPOSITE JOINT IMPLANT, internationally filed May 2, 2018, which claims benefit of priority to U.S. Provisional Patent Application No. 62/500,006, entitled, "COMPOSITE JOINT IMPLANT," filed May 2, 2017. The foregoing PCT application and provisional application are incorporated herein by reference in their entireties.

COPYRIGHT NOTICE

A portion of the disclosure of this patent document contains material which is subject to copyright protection. The copyright owner has no objection to the facsimile reproduction by anyone of the patent document or the patent disclosure, as it appears in the United States Patent and Trademark Office patent file or records, but otherwise reserves all copyright rights whatsoever.

FIELD OF THE INVENTION

The present invention relates generally to implantable composite joint implants and related methods of manufacture and use, and more particularly, to implantable composite joint implants having particular application for repairing, replacing, and/or augmenting a human joint and more specifically meniscus tissue within a human knee joint.

BACKGROUND OF THE INVENTION

The human knee joint is the most complex joint in the body and is responsible for ambulatory movement. Within the knee joint the femoral condyles and tibial plateau are separated by the medial and lateral meniscus. The meniscus is a wedge-shaped fibrocartilage tissue paired in both the medial and lateral compartments of the knee between the femur and the tibia. Macroscopically, the menisci are C-shaped (semi-lunar) tissues which feature an almost triangular (wedge shaped) cross-section, display a large curvature, and arc towards their outer circumference. These tissues cover and separate the tibial plateau from the femoral condyles providing a bearing surface within the joint and are attached to the surrounding structures in the knee joint primarily the tibial plateau. The meniscus plays a critical role in load transmission, stability and in reducing contact stresses in the knee joint which is attributed to the unique shape and microstructure of the tissue. The microstructure of the meniscus is largely comprised of type I collagen fibers and the spatial orientation of these collagen fibers are highly functionalized in order to provide the meniscus' unique mechanical properties. Specifically, the meniscus features circumferential bundles of collagen fibers embedded within a hydrated matrix which acts to bear circumferential hoop stresses. When the meniscus is axially loaded, the meniscus tends to displace radially out of the joint center due to its wedge shaped cross-section. Extrusion is, however, resisted as the meniscus is anchored both posteriorly and anteriorly in the tibia via the meniscal horns. The circumferential arrangement of type I collagen fibers throughout the meniscus as well as the meniscal horns give rise to circumferential, or hoop, stresses which resist radial displacement. The meniscus thus converts vertical load into hoop stresses, thereby reducing contact stresses by a mechanism known as the 'hoop stress mechanism'. Both menisci structures play a crucial role in knee joint function by providing joint stability, allowing shock absorption, load transmission, and stress distribution within the knee joint. Meniscal tears are the most common knee injuries with an annual reported incidence of 60-70 per 100,000 persons. With limited natural repair capabilities, surgical treatment is very common. Over 1 million surgeries involving the meniscus are performed annually in the USA. Although meniscus repair is preferred, not all meniscus tears can be repaired, such as those that occur in the avascular inner-third and complex tears that compromise the structural integrity of the meniscus. If repair is not possible, a meniscectomy is commonly used to alleviate symptoms. However, partial or total removal of the meniscus has detrimental effects on the knee joint, and these treatments increase the contact stresses on the articular surface of the knee joint. In a knee with a meniscectomy, the contact area between the tibia and the femur is reduced by 50%. Long-term, there is a high risk of osteoarthritis development after meniscectomy.

Currently, the only available treatment for a symptomatic patient who has undergone a substantial or a total meniscectomy is meniscal allograft transplantation. Meniscus allograft transplants have shown mixed results in terms of clinical improvement by reducing pain and improving function in short-term follow-ups (2 years) with long term success rates of approximately 50% within 10 years. Allograft meniscus failure is well defined and characterized as tearing and/or partial/total destruction necessitating additional surgical intervention and removal of the allograft. In addition to the long term failure rates, meniscus allografts display significantly high costs ($15K/operation), limited availability, sizing problems, risk of infection, and require challenging and complex surgery for initial implantation. Effective meniscus repair or replacement therefore plays an important role in preventing knee OA. It is this gap in the market that we seek to address through the development of a synthetic total meniscus replacement that accurately mimics the natural structure and function of meniscal tissue to provide a durable implant that can be implanted with minimal invasion and fixed securely to withstand the rigour of physical activity.

One major challenge with meniscus implants is the ability to mimic the structure-function relationship present within the native tissue and the macro-scale mechanical properties which exhibit unique tensile-compressive properties. During ambulatory movement the meniscus tissue is able to translate compressive forces into a tensile load across the meniscotibial ligaments. Current implants on the market are limited to partial meniscus replacement due to a lack of a means to mimic this functional property of force translation as well as their inability to anchor the implant within the knee joint.

To date partial meniscus implants and component meniscus systems are not able to provide the function of the native meniscus due to lack of meniscus geometry, structure and lack of an inherent attachment mechanism or ligature. To fully re-create this, meniscus implants design requires careful consideration of the shape, surface properties, inherent attachment mechanism, and bulk properties of the implant. Composite joint implants of the present invention offer reinforcement structures defined by a reinforcing (filler) phase within a polymeric matrix. The implants are characterized by properties of both the polymer matrix (material type, phases) as well as the reinforcing filler properties (orientation, volume fraction, porosity, structural arrangement, material type, etc.). Certain aspects of the composite joint implants of the present invention can be specially customized to accommodate particular load situations by modifying the filler architecture and material combinations as well as enhancing the polymeric matrix properties. Based on the limited options available for patient treatment for meniscus injuries, a composite implant for the meniscus is needed within the field.

SUMMARY OF THE INVENTION

As disclosed above, there is a need for a full-sized non-resorbable composite joint implant that can replace the function of the native meniscus while providing internal reinforcement and an inherent attachment mechanism or ligature. The present invention in some embodiments provides an implantable device for repairing, replacing, or augmenting a meniscus comprising a polymeric body, a ligature, a reinforcing element, and an encapsulation layer forming a composite joint implant. The composite joint implant in some cases mimics the anisotropic properties of the meniscus by the ligature providing a tensile bearing member and the reinforcing elements providing internal and radial support for the polymeric body.

In one aspect, the present invention provides a composite joint implant for use as a replacement for significantly damaged fibrocartilage tissue, such as meniscal tissue of the knee. The composite joint implant is constructed of non-resorbable natural and/or synthetic biomaterials that mimic the natural properties of the replaced tissue. The implant of the present invention is a natural and/or synthetic composite joint implant having a crescent-shape and the geometry of the native undamaged meniscus with internal structures embedded therein, in some cases.

According to crescent-shaped embodiments of the present invention, the composite joint implant has an anterior end, a posterior end and a middle section there between defining a curved path between the anterior and posterior ends formed from the ligature. The ligature extends circumferentially around the bulk of the composite joint implant between the anterior and posterior ends along the path of the curve and exits the anterior and posterior ends of the implant to form respective anterior and posterior attachment points.

According to a more specific embodiment of the present invention, the crescent-shaped composite joint implant is fabricated in the anatomical shape of a knee meniscus. Another embodiment of this aspect of the present invention therefore provides an artificial knee meniscus implant with a c-shaped implant having an arcuate middle section extending between an anterior end and a posterior end and reinforcing elements embedded in the composite joint implant, wherein the reinforcing elements exit each end of the implant to form respective anterior and posterior attachment points and the reinforcing element converts an axial compressive force on the implant to tensile loads on the attachment points.

According to a more specific embodiment of the knee meniscus of the present invention, at least a portion of the reinforcing element may extend along the arcuate middle section of the polymeric body in a substantially radial direction. According to an even more specific embodiment, the ligature further includes a reinforcing element embedded within the implant to prevent separation of the ligature from the polymeric body. In a preferred embodiment the composite joint implant has a wedge-shaped cross-section substantially equivalent to a human knee meniscus.

According to another embodiment of the composite joint implant of the present invention, the implant comprises a c-shaped implant having an arcuate middle section extending between an anterior end and a posterior end. A reinforcing element in addition to the ligature is embedded therein forming a scaffold. Portions of said ligature exit each end of the polymeric body to form respective anterior and posterior attachment segments to the tibia which extends parallel to a central axis of the implant. The reinforcing element is configured to convert an axial compressive force on said implant to tensile loads on said attachment points. Optionally, portions of the reinforcing element also can exit the polymeric body, optionally to form attachment points with the ligature or independently of the ligature.

According to another more specific embodiment of the composite joint implant of the present invention, the inventive implants have at least one peripheral attachment point. In a preferred embodiment, at least one peripheral attachment point coincides with a point at which the circumferential ligature intersects with the reinforcing element. In another preferred embodiment, the reinforcing element extends throughout the wedge-shaped cross section of the middle section of the polymeric body.

According to another more specific embodiment of the composite joint implant of the present invention, the reinforcing element extends beyond the circumference of the composite joint implant providing peripheral attachment by any means of adjoining the reinforcing element to surrounding tissues in the knee joint. In another preferred embodiment, the reinforcing element extends beyond the circumference of the composite joint implant and can be attached to the tibial plateau of the subject receiving the composite joint implant. In another preferred embodiment, the reinforcing element that extends beyond the circumference of the composite joint implant is not covered with the encapsulation layer.

In any of the inventive embodiments at least one of the implant, the circumferential ligature or the reinforcing element may be formed from a material selected from proteins, proteoglycans, biocompatible synthetic polymers and combinations thereof. In some embodiments the material is non-resorbable. In any of the inventive embodiments at least one of the implant, the circumferential ligature or reinforcing element is formed from a biocompatible synthetic polymeric material. In some embodiments the polymeric material is non-resorbable.

According to another aspect of the present invention, a method is provided for replacement of a damaged knee meniscus. Methods according to this aspect of the present invention include the steps of:

replacing a damaged meniscus with a composite joint implant according to the present invention by removing the damaged meniscus tissue by inserting a composite joint implant according to the present invention, having anterior and posterior attachment points, between the tibial plateau characterized by having anterior and posterior ends inserted therein, and the corresponding femoral condyle; and securing the anterior and posterior ends of the implant to the corresponding anterior and posterior with two trans-osseous tunnels which the ligature can be passed through and secured in place using interference screws or other fixation tools.

According to yet another aspect of the present invention, a method is provided for fabricating an anatomical composite joint implant to replace a human meniscus. In another preferred embodiment, the composite joint implant replaces a medial or a lateral human meniscus. In certain instances, three-dimensional images of human joints, taken with magnetic resonance imaging (MRI) for example, can aid in the anatomical design and manufacture of an embodiment of the present invention. In this way, a composite joint implant of the present invention can exhibit an anatomical meniscus shape. In further embodiments, it can be said that a composite joint implant has a crescent shape. In still other embodiments, a composite joint implant can exhibit a semilunar shape.

Methods according to this aspect of the present invention include the steps of:

forming a ligature with at least one fiber; and embedding the ligature into a polymeric body, wherein the body has a crescent middle section extending between an anterior end and a posterior end; and wherein the ligature exits each end of the body forming a construct. The periphery of the construct is then covered with the encapsulation layer to form the composite joint implant.

By creating a composite joint implant that has the structure, mechanics, and geometry as that of the normal tissue, the function of the natural tissue can be replicated. As the composite joint implant is non-resorbable it is able to withstand the biomechanical forces and environment upon implantation.

In some embodiments the polymeric body is shaped and molded from a polymeric material forming semi-circular or trapezoidal geometry. In some embodiments the body is comprised of a wedge-shaped cross-section. The polymeric body can be formed from compression molding, injection molding, casting, machining, assembly, additive manufacturing, or other forming processes known in the field. The polymeric body features a concave top surface, a flat convex bottom surface, an internal edge wherein the top surface and bottom surface meet. In some embodiments the top surface and the bottom surface can feature a roughened surface with a roughness value greater than 1 micron. In more preferred embodiments the top surface and the bottom surface can feature a roughened surface with a roughness value greater than 10 microns.

The polymeric body features a wedge-shaped cross-section wherein the top surface and bottom surface expand away from each other increasing the thickness of the device towards the outer periphery of the composite joint implant. The external edge of the polymeric body further features a recess or groove, in some embodiments. The recess is positioned around the periphery of the polymeric body and spans at least a portion of the thickness of the composite joint implant along the external edge. The recess can feature a varying depth into the thickness of the polymeric body towards the internal edge wherein the top surface and the bottom surface of the polymeric body meet. The recess can be comprised of a protruding lip on either the top surface, the bottom surface, or both surfaces. The protruding lips of the cavity can be separate or connected by a plurality of polymeric columns forming a plurality of apertures and/or openings. The plurality of apertures can be varying size, geometry and density around the perimeter of the polymeric body. Overall the recess of the body provides a "lock-and-key" mechanism for the ligature component and prevents circumferential bulging and detachment of the ligature around the polymeric body.

The ligature is formed in a separate manufacturing process from the polymeric body, in some instances. The ligature is comprised of a tape-like, rope-like, or tube-like geometry. In some embodiments the ligature can wrap around the external edge of the polymeric body. In some embodiments the ligature can surround a portion of the available surface area of the polymeric body. In some embodiments the ligature can surround the majority of the available surface area of the polymeric body. In some embodiments the ligature can be comprised of a varying cross-sectional area around the periphery of the polymeric body. In some embodiments the ligature can display a change in orientation around the polymeric body by greater than 90°.

In some embodiments the ligature can be constructed from a plurality of fibrous materials where a fiber can be defined as having an aspect ratio (length/diameter) greater than 100. The fibers used herein can be constructed from singular or multiple materials, and can feature different fiber deniers (linear density of fiber reported in grams/9000 meters), sizes, and geometries. Additionally the fiber design can be engineered to include such fiber geometries as core-sheath, islands in the sea, pie cross-section, bi-lobal, tri-lobal, among others. In some embodiments the ligature can be comprised of a variety of materials including polyesters, polyethylenes, polyolefins, poly(ether ether ketones), poly(urethanes), protein-based materials, polysaccharide based materials and any combination thereof.

In some embodiments the ligature can be designed to fit intricately around and within the external edge of the polymeric body. As described above, the polymeric body can be shaped to provide a recess wherein the ligature can be threaded through or within the body to allow integration of the polymeric body with the ligature. The ligature can be comprised of a woven structure, knitted structure, tape-like structure, braided structure, or plurality of fibers aligned along their long axis around the periphery of the polymeric body. In some embodiments the ligature can be threaded in an intertwining or alternating pattern in the cavity of the polymeric body. It can be said that the ligature has a long axis, extending from the anterior end to the posterior end. This is true even when the ligature defines a curve between those ends.

In some embodiments, the ligature or scaffold ends extend out of one or both of the two ends of the mold during manufacturing of the polymeric body or during encapsulation to allow for the ligature or scaffold to be fixed to the bone.

In some embodiments the ligature features high stiffness and high strength, with low stretch properties. Stiffness can be inferred as tensile modulus and a common unit of measure is mega-pascals (MPa). Strength can be inferred as ultimate tensile strength and a common unit of measure is MPa. Stretch can be inferred as strain at break and is reported as a percent of the difference of the elongated deformation comparative to the original length of the material. In some embodiments the ligature can form a tube-like construct and can encapsulate an entire polymeric body. The ligature can be comprised of a varying cross-sectional area that is expandable and collapsible around the polymeric body. In some embodiments the ligature can also be comprised of a tube-like structure with varying wall thickness.

In some embodiments the ligature can be comprised of a variety of materials and can feature a coating which encapsulates or surrounds each individual fibrous element within the engineered bulk of the ligature. This encapsulation material can be comprised of a material with a lower melting temperature ($T_m$) comparative to the bulk material of the ligature. In some embodiments the coating material can be comprised of a material with a higher $T_m$ comparative to the bulk polymer of the ligature. In some embodiments the coating material can be comprised of a material with a similar $T_m$ comparative to the bulk material of the ligature.

In some embodiments the ligature can be comprised of two different fibrous materials wherein one fibrous material comprises a minor component of the ligature. A minor component can be defined as less than 50% of the mass of the ligature is comprised of that material, where a major component of the ligature is comprised of 50% or more of the mass. In some embodiments the minor component of the ligature is comprised of a lower $T_m$ material comparative to the major component of the ligature. In some embodiments the ligature can be coated by an encapsulation material prior to assembly into an engineered construct. In some embodiments the ligature can be coated prior to assembly with the polymeric body. In some embodiments the ligature can be coated after combination with the polymeric body. In some embodiments the ligature can be coated before and during assembly with the polymeric body. Suitable encapsulation materials for the ligature include, but are not limited to, polycarbonate urethane, a polyvinyl alcohol, polyethylene glycol or a combination thereof. The ligature can be comprised of elongated ends which extend beyond the polymeric body. In some embodiments, the ends of the ligature can feature an increase in rigidity or tensile modulus compared to the central region of the ligature. Additionally, the ends of the ligature can feature placement of ladder-rung components to increase contact area and match mechanical properties of human bone. The ladder-rung components can be comprised of fibrous elements or can be produced from a solid polymeric, inorganic, or composite entity. Fibrous elements for the ladder-rung component can be comprised of high denier fibers or yarns to create a protrusion above the main plane of the ligature. Such fibrous elements can be formed by alternating the denier of the yarn or fiber used in the production of the ligature. Such processes include varying this input either in woven, weft knit, warp knit or braiding by varying input yarns into the manufacturing process. Additionally the ladder-rung components can be comprised of pre-formed solid polymeric components. The pre-formed solid polymeric components can be polygonal in cross-section and extend beyond the width of the ligature. The ladder-rung components of pre-formed solid polymeric components can be attached by any means such as sewing, gluing, sonic welding laminating, printing, additive manufacturing or any combination thereof. In one embodiment the ligature is produced with a repeating series of loops for incorporating the ladder-rung components directly into the ligature. As a part of the ligature the ladder-rung components can feature periodicity in regards to placement on the ends of the ligature. The ladder-rung components can feature on one, both, or none of the ends of the ligature. The ladder-rung components can also vary in terms of pitch, size, density, and cross-sectional area. In some embodiments, these ends of the ligature can feature a change in geometry and orientation with respect to the polymeric body. The ligature can feature engineered porosity along the length, in particularly in contact with the polymeric body to promote integration between the polymeric body and the encapsulation material.

In some embodiments the implant is further comprised of an encapsulation material that surrounds the polymeric body periphery and the ligature. In some embodiments the encapsulation layer impregnates the ligature and intricately adjoins the ligature with the polymeric body. In some embodiments the minor component of the ligature has the same composition as the encapsulation layer. In some embodiments the encapsulation layer is the same composition as the polymeric body. In some embodiments, the encapsulation layer, minor component of the ligature, and polymeric body are of the same composition.

In certain instances, the top and bottom surfaces of the implant are further coated with a lubricious coating. The lubricious coating can cover none, a portion, or all of the articulating surfaces. Lubricious coatings can employ any suitable material, such as, for example, perhalogenated polyolefins, hyaluronan, polyethylene glycol, polyethylene oxide, polyvinyl alcohol, or copolymers therein. In some cases, the lubricious coating employs a polar substance. In other cases, the lubricious coating comprises an anionic substance.

The composite joint implant can be constructed from any suitable materials. In some cases, the present invention can be constructed from a range of known materials in a film, fiber, foam, molded structure or fabric format wherein the film, fiber, foam or fabric is comprised of polyethylene, ultra-high molecular weight poly(ethylene), poly(ethylene terephthalate), poly(propylene), polyvinyl alcohol, poly (ether urethane urea), poly(carbonate urethanes), silicones, nylons, polyamides, among others. The implantable device comprises, in certain instances, a non-degradable material that has an ultimate elongation (%) of 1-1,000 percent strain with an ultimate tensile strength 1-5,000 MPa.

Suitable non-degradable polymers for the attachment include polyethylene, polystyrene, silicone, polyfluoroethylene, a polyamide (e.g., nylon), polycarbonate, polysulfone, polyurethane, polybutadiene, polybutylene, polyethersulfone, polyetherimide, polyphenylene oxide, polymethylpentene, polyvinylchloride, polyvinylidene chloride, polyphthalamide, polyphenylene sulfide, polyetheretherketone ("PEEK"), polyimide, polymethylmethacylate, polyester terephthalate, polypropylene, and any combination thereof.

The ligature may also include inherent fixation mechanism to attach to tissue within the human body. The implant is implanted using standard arthroscopic techniques. A guide is drilled through the tibia with overdrill using a reamer on the tibia to tibial attachment area of meniscus horns. The implant is then secured using interference screws, with the ENDOBUTTON® technique, or similar method.

In certain embodiments the ligature can be comprised of protrusions that increase the surface area and contacting surface of the ligature. The protrusions can be comprised of a ladder rung morphology on the ends of the ligature.

The polymeric body is sized and shaped to mimic a portion of the medial or lateral meniscus. The polymeric body can have inherent porosity and mechanics to mimic the properties of the native meniscus. In certain embodiments the ligature and reinforcing element is able to partially and/or completely encapsulate the polymeric body, and is compatible with the encapsulation layer. In a preferred embodiment the ligature is composed of three regions; two end sections designed for attachment of the device at the site of implantation, which allows for bone tissue integration, and a central region which serves as a means to incorporate the attachment with the polymeric body. The central region of the attachment differs from the two end-regions in size, fiber angle, geometry, porosity and/or polymer composition or it may be one continuous structure with the two end regions for attachment and fixation.

According to the aspect of the present invention, the combination of the ligature, polymeric body, reinforcing element, and encapsulation layer can be maximized by chemical/physical bonding of these entities.

According to the aspect of the present invention the composite joint implant is manufactured using additive manufacturing technologies. In yet another embodiment the composite joint implant may be a meniscus implant for a knee joint.

In another preferred embodiment the composite joint implant is manufactured using at least two materials which are fabricated sequentially, locally, or combinations thereof. As used herein, regionally indicates a large area of the implant, locally defines a smaller region of the composite joint implant.

The above-mentioned and additional features of the present invention and the manner of obtaining them will become apparent, and the invention will be best understood by reference to the following more detailed description. All references disclosed herein are hereby incorporated by reference in their entirety as if each was incorporated individually. This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter. The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF DRAWING FIGURES

The accompanying drawings, which are incorporated herein and form a part of the specification, illustrate some, but not the only or exclusive examples of embodiments and/or figures. It is intended that the embodiments and figures disclosed herein are to be considered illustrative rather than limiting. In the drawings.

FIG. 12a-b are diagrammatic views of a scaffold designed from a ligature adjoined to a reinforcing element including a cross-sectional view (b) of the scaffold.

FIG. 13a-d are diagrammatic views of a scaffold designed from a ligature and reinforcing element intricately connected together along with varying modes for the cross-sectional view of the scaffold (b-d) where inset images c and d illustrate the location of an internal polymeric body.

FIG. 14a-b are diagrammatic views of a scaffold designed from a ligature and reinforcing element intricately connected together along with a cross-sectional image of the scaffold (b).

Figure 15:
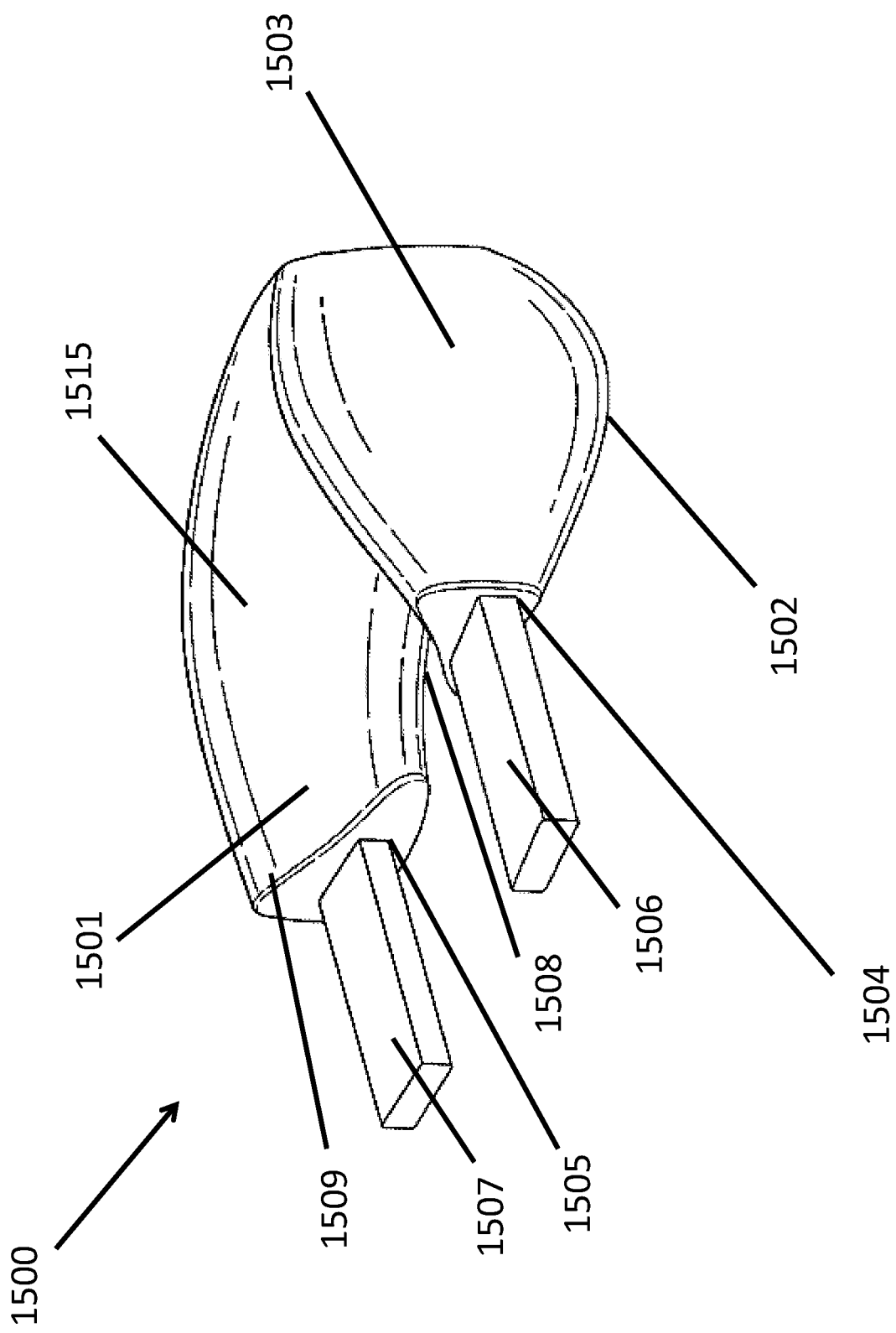

FIG. 15 is a diagrammatic view of a composite joint implant illustrating the encapsulation layer.

Figure 16:
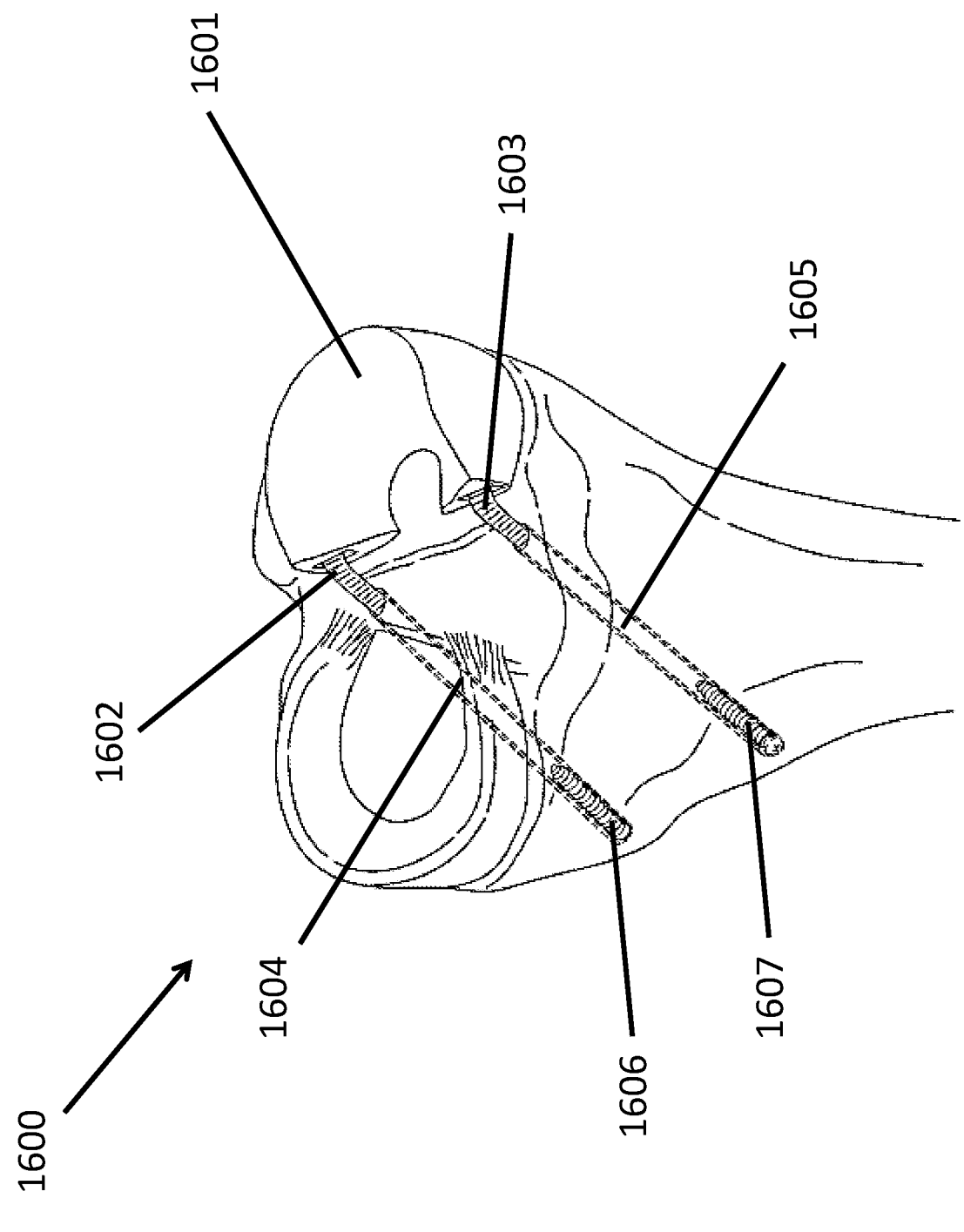

FIG. 16 is a diagrammatic view of a composite joint implant attached and fixed to a subject's tibial plateau with transosseos attachments.

Figure 17:
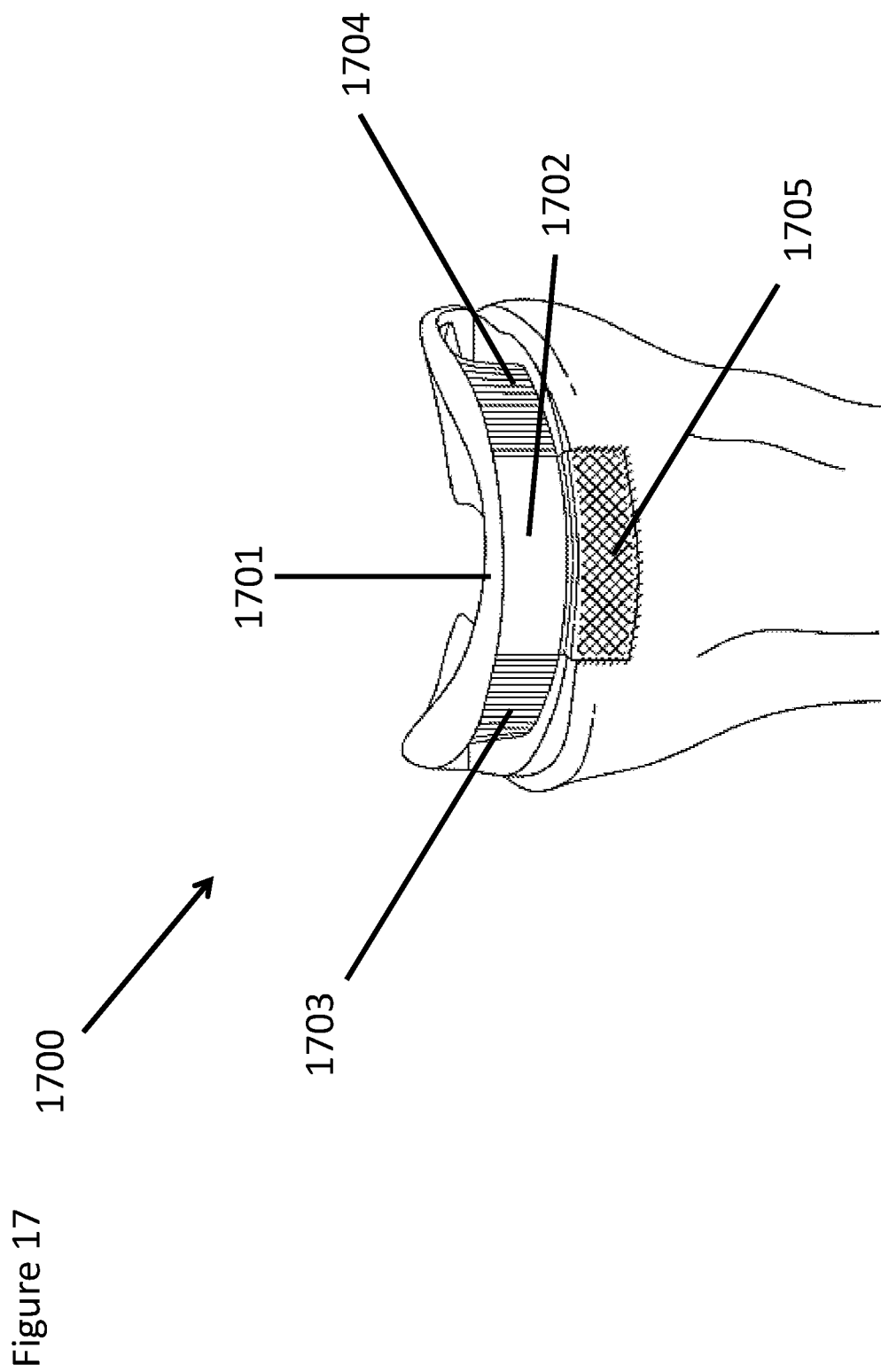

FIG. 17 is a diagrammatic view of a composite joint implant attached and fixed to a subject's tibial plateaus with peripheral attachment.

Figure 18:
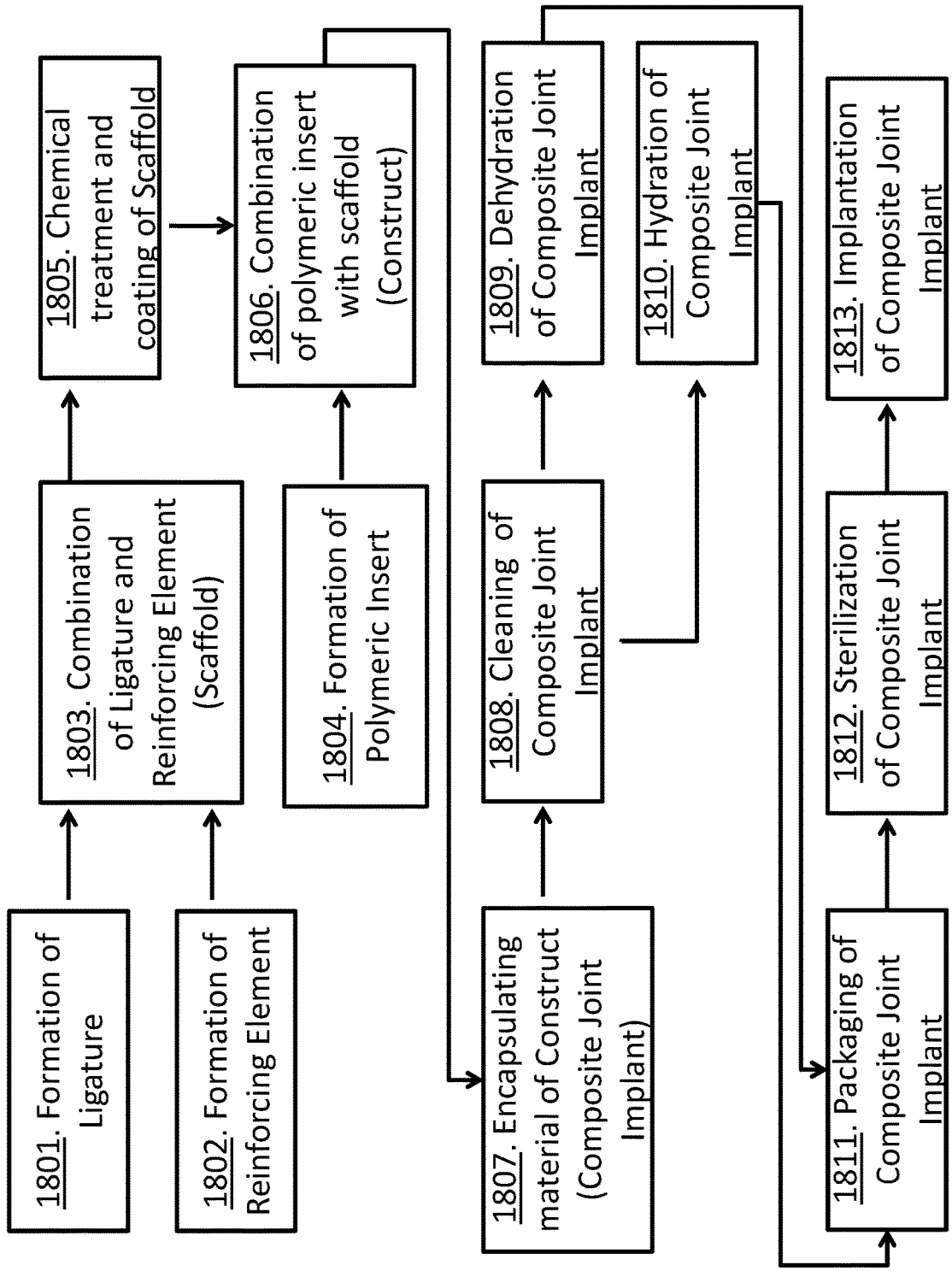

FIG. 18 is a flow chart of the manufacturing technique including manufacturing of the ligature, reinforcing element and polymeric body in separate process steps.

Figure 19:
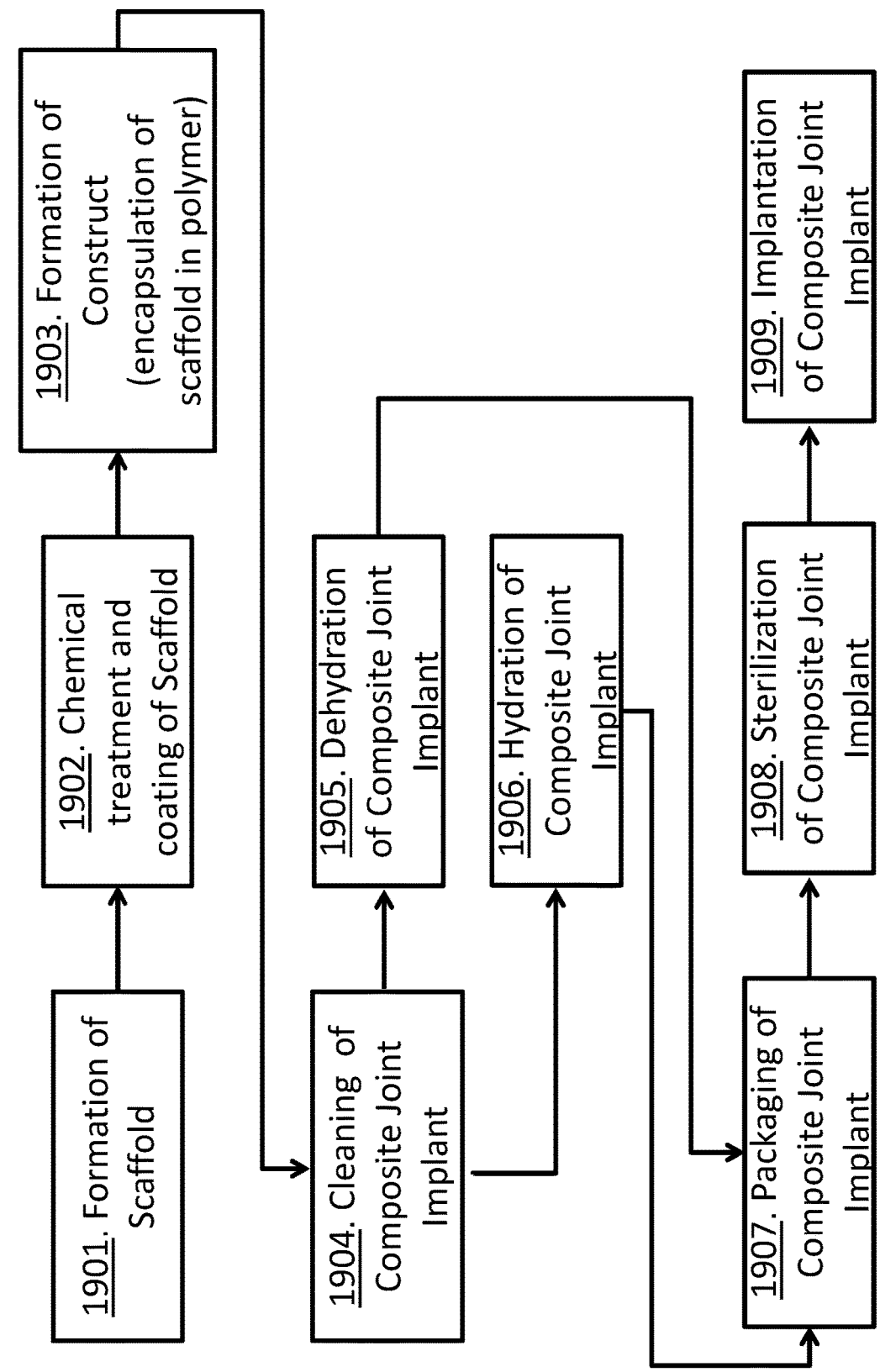

FIG. 19 is a flow chart of the manufacturing technique including formation of the scaffold and formation of the construct in single process steps.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF THE INVENTION

Due to the significant drawbacks present within the field of the invention, at least some of the embodiments of the present invention offer significant advantages and improvements in the field. In order to repair or reconstruct an extensively damaged meniscus or where a meniscus is lost in its entirety, a technique may be used wherein a composite joint implant material is implanted in order to replace the damage or lost meniscus. This process of meniscus repair and/or construction requires removal of any remaining meniscal tissue to provide space for the composite joint implant. The composite joint implant may need to be shaped to match the missing meniscus and is implanted in the knee joint to replace the meniscus. The composite joint implant and method of the present invention provides for meniscus repair/replacement while providing full meniscal functionality which includes maintenance of the hoop-stress resistance to protect the joint surfaces of the femoral condyles and tibial plateau in the knee joint. Before explaining the present invention in detail, it should be noted that the invention is not limited in its application or use to the details of construction and arrangement of parts illustrated in the accompanying drawings and description. Referring to FIGS. 1-19 certain embodiments of the present invention will now be described in detail.

The methods described herein are by no means all-inclusive, and further methods to suit the specific applications as contemplated herein will be apparent to the ordinary skilled artisan.

Definitions

As used herein, each of the following terms has the meaning associated with it in this section. The articles "a" and "an" are used herein to refer to one or to more than one (i.e. to at least one) of the grammatical object of the article. By way of example, "an element" means one element or more than one element. The term "about" will be understood by persons of ordinary skill in the art and will vary to some extent on the context in which it is used.

The term "monomer" as used herein refers to a small molecule and is the primary building block and structural repeat unit for polymers (defined below). Monomers can possess a variety of chemistries and can undergo chemical reaction in the presence of an initiator and catalyst.

The term "polymer" as used herein refers to a large molecule (macromolecule) composed of repeating structural units often connected by covalent chemical bonds. Polymers may be natural or synthetic. Polymer nomenclature is generally based upon the type of monomer residues comprising the polymer. Polymers that contain only a single type of repeat unit are known as homopolymers, while polymers containing a mixture of repeat units are known as copolymers.

The term "polymeric body" as used herein refers to a solid structure comprised of a network of oligomers or polymer chains that are water-insoluble. The polymeric body can be produced from reaction of monomeric materials, oligomeric materials, and or polymeric materials. Polymeric body can be formed by free radical polymerization, injection molding, compression molding, casting, additive manufacturing techniques, physical molding, among others. The polymeric body can be comprised of polymers and copolymers. The polymeric body can feature varying geometries and mimics the structure and compressive mechanics of meniscus tissue. Compressive modulus of the polymeric body refers to the stiffness of the polymeric body when placed under an axial deforming load or force. In some embodiments, the polymeric body defines a recess, for example, in which the ligature may be disposed; in other embodiments, the polymeric body does not define a recess, and the polymeric body is enclosed by other structures, such as, for example, a scaffold.

The term "fiber" as used herein refers to a class of materials that are continuous filament or are in discrete elongated pieces and are characterized by a an aspect ratio (length to diameter ratio of 10:1 and more preferably 100:1. They can be used as a component of a ligature or reinforcing element by being manipulated to form a structure through manufacturing via cross-linking, gluing, roping, plying, weaving, braiding, knitting, knotting, stitching, molding among others.

The term "yarn" as used herein refers to a class of materials that are continuous filaments or are in discrete elongated pieces that are comprised of more than one end and are formed from a plurality or bundle of filaments grouped together. Yarns can be characterized by their denier defined as linear density grams per 9,000 meters, and strength properties defined as tenacity which is the tensile load in Newtons (N) or gram-force divided by the denier. High tenacity means a tenacity of ≥5 $g_f$/denier. Strain at break is defined as the maximum extension undergone during a tensile test.

The term "ligature" as used herein means a tensile bearing material, optionally formed from a combination of materials including fiber and/or yarn, that provides circumferential reinforcement and implant fixation, for example, to the tibia. The ligature can be formed from a variety of manufacturing methods included weft knitting, warp knitting, braiding, weaving, bundling, knotting, looping, among others. Ligature can be further defined by mechanical properties such as tensile strength reported in maximum load (N) or megapascal (MPa) or strain at break, as well as physical properties such as thickness, areal density, length, width, and surface roughness, among others.

The term "reinforcing element" as used herein means a tensile bearing material that is formed from a fiber, a yarn, or a combination of fibers, yarns, or both fibers and yarns. The reinforcing element supports the polymeric body in compression and assists in preventing radial destruction along with translation of the compressive mechanical forces from the polymeric body to the ligature of the composite joint implant. The reinforcing element can be formed from a variety of manufacturing methods included weft knitting, warp knitting, braiding, weaving, bundling, knotting, looping, additive manufacturing, among others. Reinforcing element can be further defined by mechanical properties such as tensile strength reported in maximum load (N) or mega-pascal (MPa) or strain at break, as well as physical properties such as thickness, areal density, length, width, and surface roughness, among others. The ligature and the reinforcing element differ structurally in some embodiments as the ligature is comprised of a higher areal density (i.e. linear mass), lower porosity (i.e. material openness), higher thickness, while the reinforcing element is of a more open, porous nature that is comprised of a lower areal density and in some embodiments a larger volume.

The ligature and reinforcing element can be distinguished by their function in the joint. The ligature's primary role is to hold the composite joint implant in place in the joint, and to resist those forces that would dislodge the entire implant out of place. The reinforcing element's primary role is to maintain the structural integrity of the composite joint implant against the considerable compressive forces present in the joint. In some cases, a scaffold performs the functions of a ligature and a reinforcing element.

The term "scaffold" as used herein means a combination of both the "ligature" with the "reinforcing element". The scaffold can be formed by any means of adjoining the ligature with the reinforcing element wherein the ligature and the reinforcing element are fabricated in different manufacturing process steps and a third process is used to form the scaffold. The scaffold can be produced in a singular process where both the ligature and the reinforcing element are formed in the same manufacturing process step. The scaffold can mimic the size and shape of a meniscus.

The term "construct" as used herein means a combination of the "scaffold" with a "polymeric body" wherein the reinforcing elements of the formed scaffold interact with and support the polymeric body. The construct can resemble the function, shape and size of a meniscus. In some cases, the term "implant" as used herein means the "construct" combined with the encapsulation material. In other cases, the term "implant" means a device suitable for insertion into a joint in need thereof, and may comprise one or more of the ligature, polymeric body, reinforcing element, and encapsulation material. The encapsulation material can be added in an additional manufacturing step wherein the exposed ligature surrounding the polymeric body is covered by the same or a different polymeric material during an over-molding or over-casting process, sealing off the ligature in the implant. The implant can also be produced in a single manufacturing process wherein the scaffold, held in tension around protruding pins within the mold or by other means to prevent any slack in the scaffold, is fully encapsulated in the polymer in the same manufacturing process step. In some embodiments, the encapsulation material completely covers the polymeric body, more specifically the top and bottom surfaces and the internal edge and periphery of the polymeric body. An additional layer or coating with a lower surface roughness or a more lubricious chemistry can be applied to the top and bottom surfaces of the implant to enhance the tribological properties of the implant resulting in reduced friction and wear for the application. The implant mimics the size, shape, mechanical, and tribological properties of a native meniscus. The implant is a composite by structure formed from the varying components and assembled into a composite. As used herein, "the vertical axis" indicates the direction of gravity if the composite joint implant were positioned in a joint of a subject while standing. For a meniscal implant, the vertical axis corresponds to the direction compressive forces would exert on the composite joint implant, as the implant cushions the interface between the femoral bone and the tibial plateau.

The term "subject" as used herein refers to any living animal, preferably a mammal and more preferably a human. The composite joint implant as described herein are designed for implantation within a Subject in need thereof.

Based on the limitations with meniscus treatments, the present invention offers significant improvement to the fields of meniscus replacement and repair. The present invention provides the design and combination of multiple components to form a composite joint implant that more accurately mimics the natural structure-function properties of the native meniscus. Relevant design factors for the composite joint implant include 1) polymeric body that provides the structure and base mechanical properties, 2) ligature to provide tensile-load bearing component and a means of attaching the composite joint implant to the body, 3) reinforcing elements to further support radial distortion of the polymeric body and assist in load transfer from the polymeric body to the ligature, and 4) articulating surface coating for enhanced wear properties if required.

Figure 1:
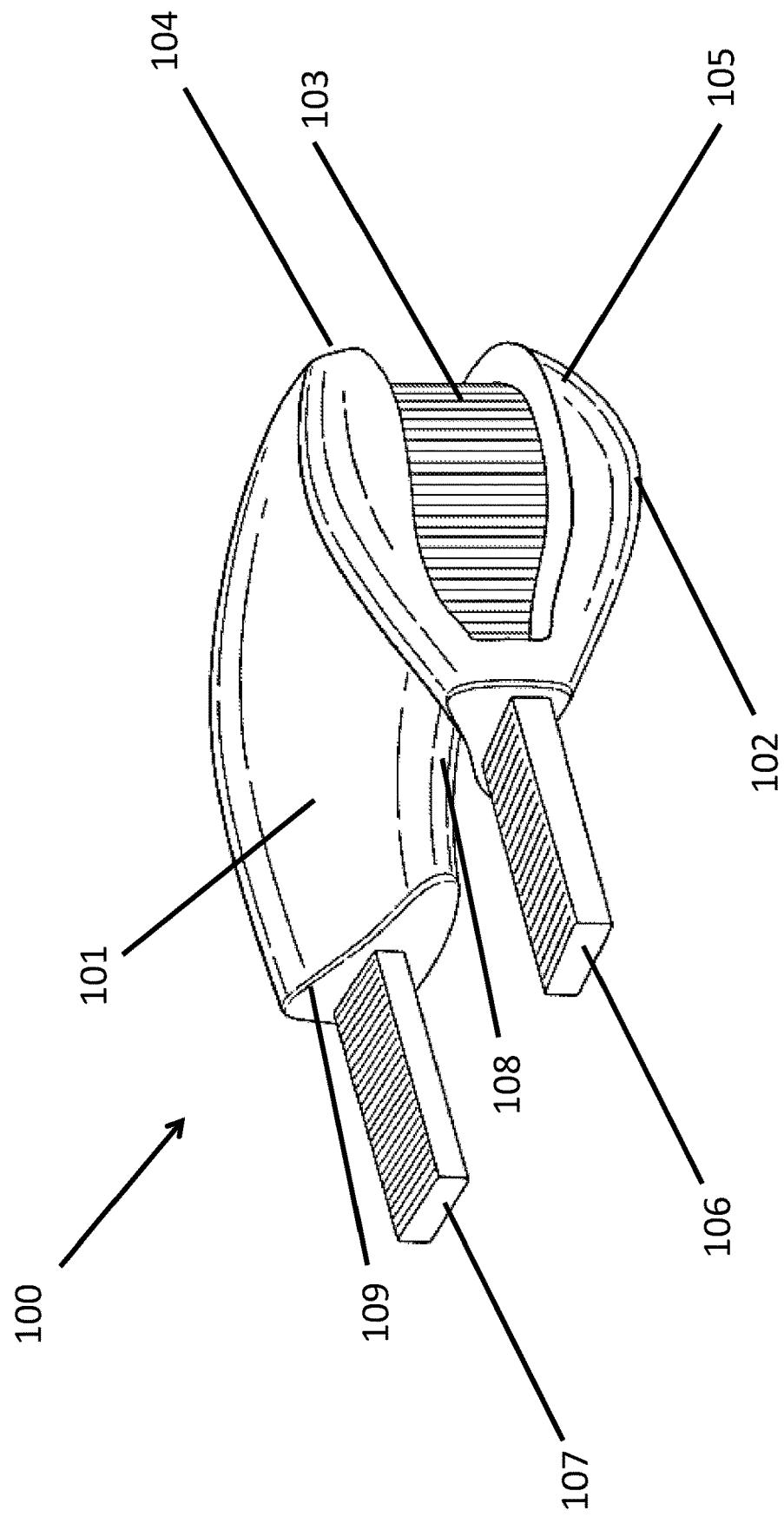
FIG. 1 is a diagrammatic view of a composite joint implant.

As an illustrative embodiment of the invention as shown in FIG. 1, a composite joint implant (100) can be designed by combination of a polymeric body, ligature and optionally a reinforcing element. The composite joint implant can be designed by reference to the structure and organization of meniscus tissue. The composite joint implant (100) includes a top surface (101), and a bottom surface (102), that is separated by a ligature (103) that conforms to the recess of the composite joint implant (100). The ligature (103) is retained by a top lip (104) and bottom lip (105) of the composite joint implant. The ligature (103) extends through and beyond the composite joint implant with the ligature forming an anterior end (106) and a posterior end (107). The composite joint implant can be designed to have a wedge-shaped cross-section wherein the top surface (101) meets the bottom surface (102) forming an internal edge (108). The composite joint implant is further defined by a lubricious coating (109) which covers a portion of the composite joint implant.

Figure 2:
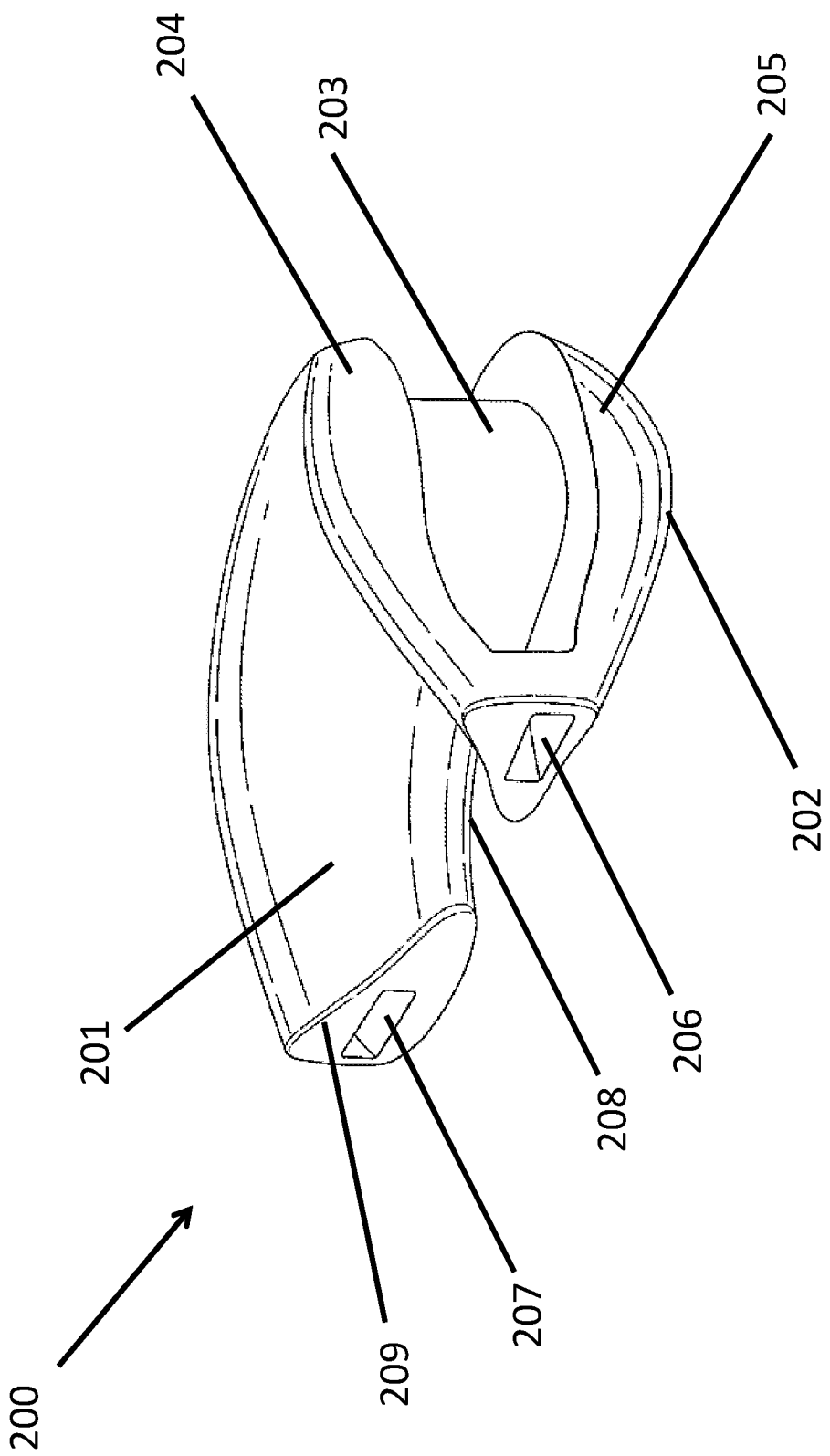
FIG. 2 is a diagrammatic view of a polymeric body of the composite joint implant.

As illustrated in FIGS. 2-5 the polymeric body can feature many modes along with expansive features to mimic the majority of the meniscus tissue. FIG. 2 shows a diagrammatic view of the polymeric body (200) wherein the polymeric body is wedge-shaped in cross-section and is comprised of a polymeric material. Referring to FIG. 2, the polymeric body has a top surface (201) that terminates in upper lip (204), and a bottom surface (202) that terminates in bottom lip (205). The polymeric body curves and extends into an anterior opening (206) and a posterior opening (207). The outer periphery of the polymeric body (200) features a recess or cavity (203) for placement of the ligature. In some embodiments the recess (203) has a similar cross-sectional geometry to that of the ligature. In more preferred embodiment the cross-section of the recess is semi-circular, square, rectangular, or polygonal. The recess (203) surrounds the majority of the polymeric body (200) and forms the anterior opening (206) and the posterior opening (207). The anterior opening (206) and posterior opening (207) can be shaped to match the cross-section of the ligature and provide an exit point for the ligature. In some embodiments the anterior opening (206) and/or posterior opening (207) can have the same or different cross-sections. The top surface (201) of the polymeric body has a concave surface and the bottom surface (202) of the polymeric body is relatively convex. Based on its orientation in the joint, the top surface (201) of the polymeric body (200) is designed to engage with the femoral condyle of a human. The bottom surface (202) of the polymeric body (200) is designed to engage with the tibial plateau of a human. The polymeric body (200) is comprised of an internal edge (208) where the top surface (201) and bottom surface (202) meet on an internal edge (208). The openings (206 and 207) of the polymeric body can exhibit any suitable alike or different cross-sectional geometries. Those openings (206 and 207) restrict the range of motion of the ligature while allowing the ligature to extend beyond either end of the polymeric body (200). In this embodiment, lubricious coating (209) imparts a lower surface roughness to the top surface (201) and the bottom surface (202) of the polymeric body (200). In certain embodiments, the design of the composite joint implant (100) will determine the orientation and placement position of the device into the defected joint area.

Figure 3:
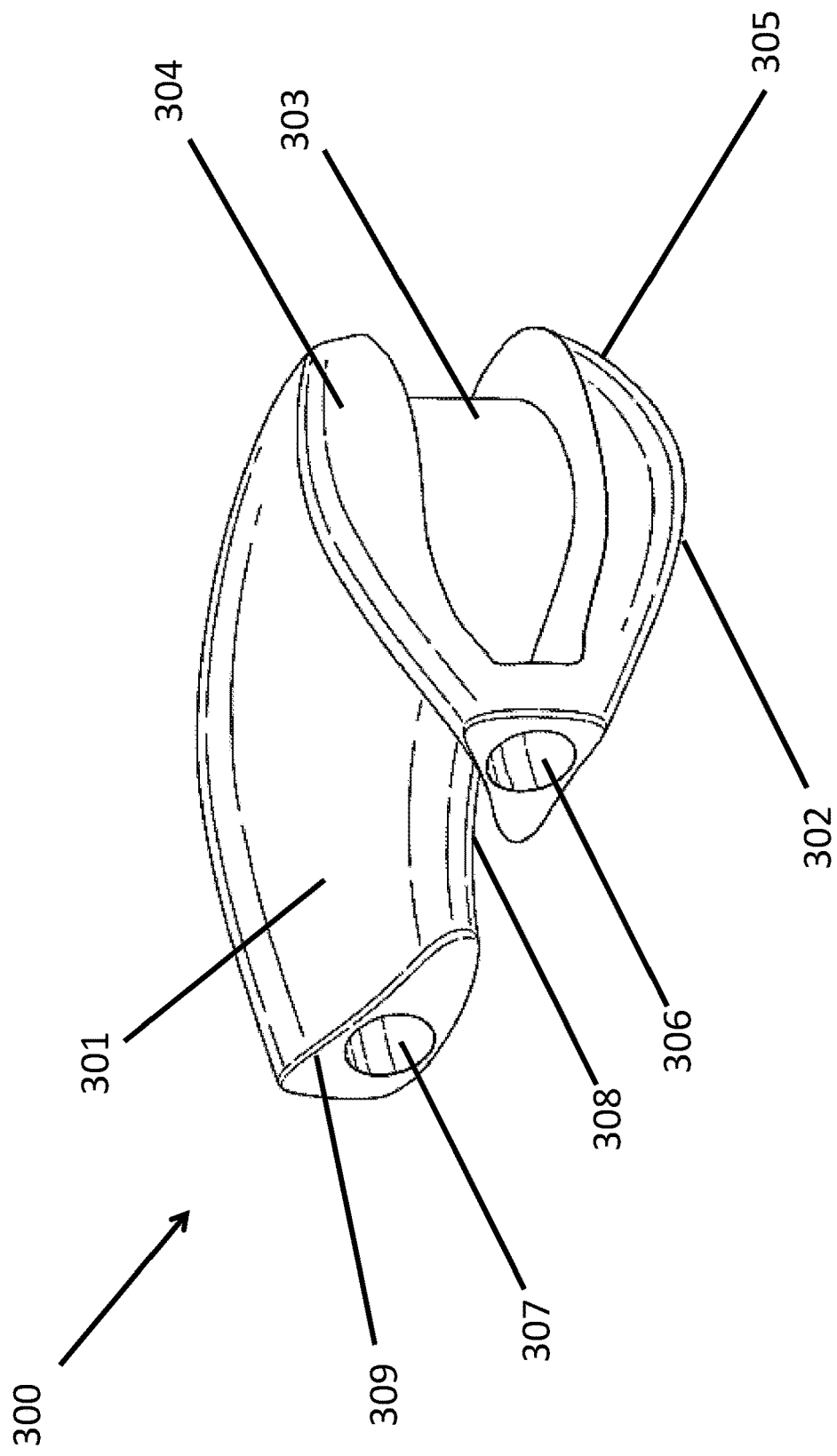
FIG. 3 is another diagrammatic view of a polymeric body of a composite joint implant illustrating how the posterior and anterior opening can have different geometry compared to the peripheral recess.

In reference to FIG. 3, the polymeric body (300) can feature posterior opening (307) and anterior opening (306) of different geometry compared to the peripheral recess (303) formed by the top lip (304) and bottom lip (305) of the polymeric body (300). Top surface (301) meets bottom surface (302) at internal edge (308), imparting a wedge-shaped cross section to polymeric body (300). Lubricious coating (309) imparts a lower surface roughness to top surface (301) and bottom surface (302).

Figure 4:
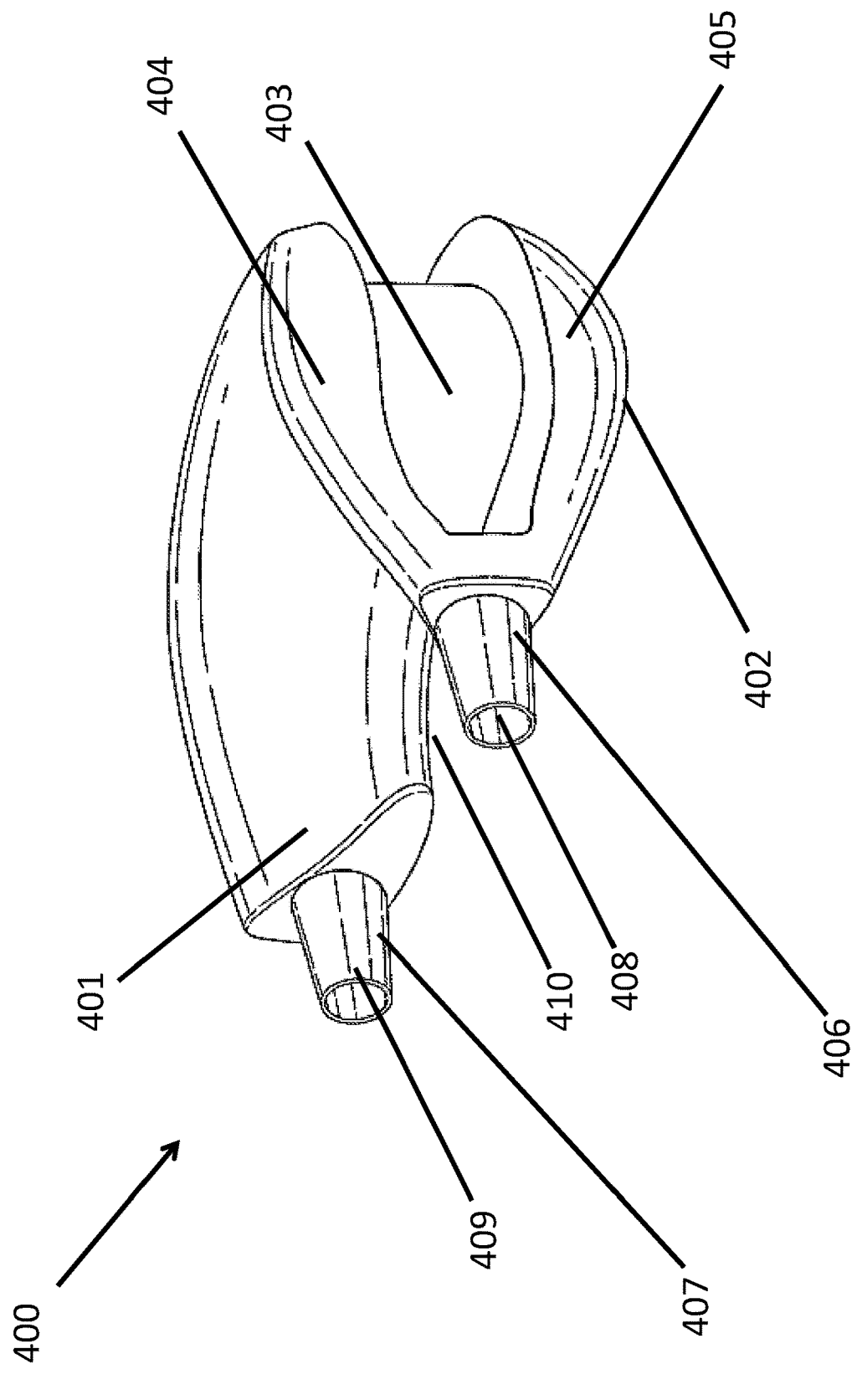
FIG. 4 is another diagrammatic view of a polymeric body of a composite joint implant illustrating how the posterior and anterior opening can extend beyond the polymeric body and have different geometry compared to the peripheral recess.

In reference to FIG. 4, the polymeric body (400) can be comprised of anterior horn (406) and a posterior horn (407) that extend beyond the body of the polymeric body (400). The anterior horn (406) and posterior horn (407) can form a hollow structure, which can resemble a tubular geometry. The horns (406 and 407) are comprised of a thin wall that can be conforming and flexible. The horns (406 and 407) provide an opening (408 and 409) for the ligature to extend beyond the polymeric body (400). Top surface (401) meets bottom surface (402) at internal edge (410), imparting a wedge-shaped cross section to polymeric body (400). Top surface (401) terminates in top lip (404), and bottom surface terminates in bottom lip (405), and define recess (403), adapted to encompass a ligature (not shown).

Figure 5:
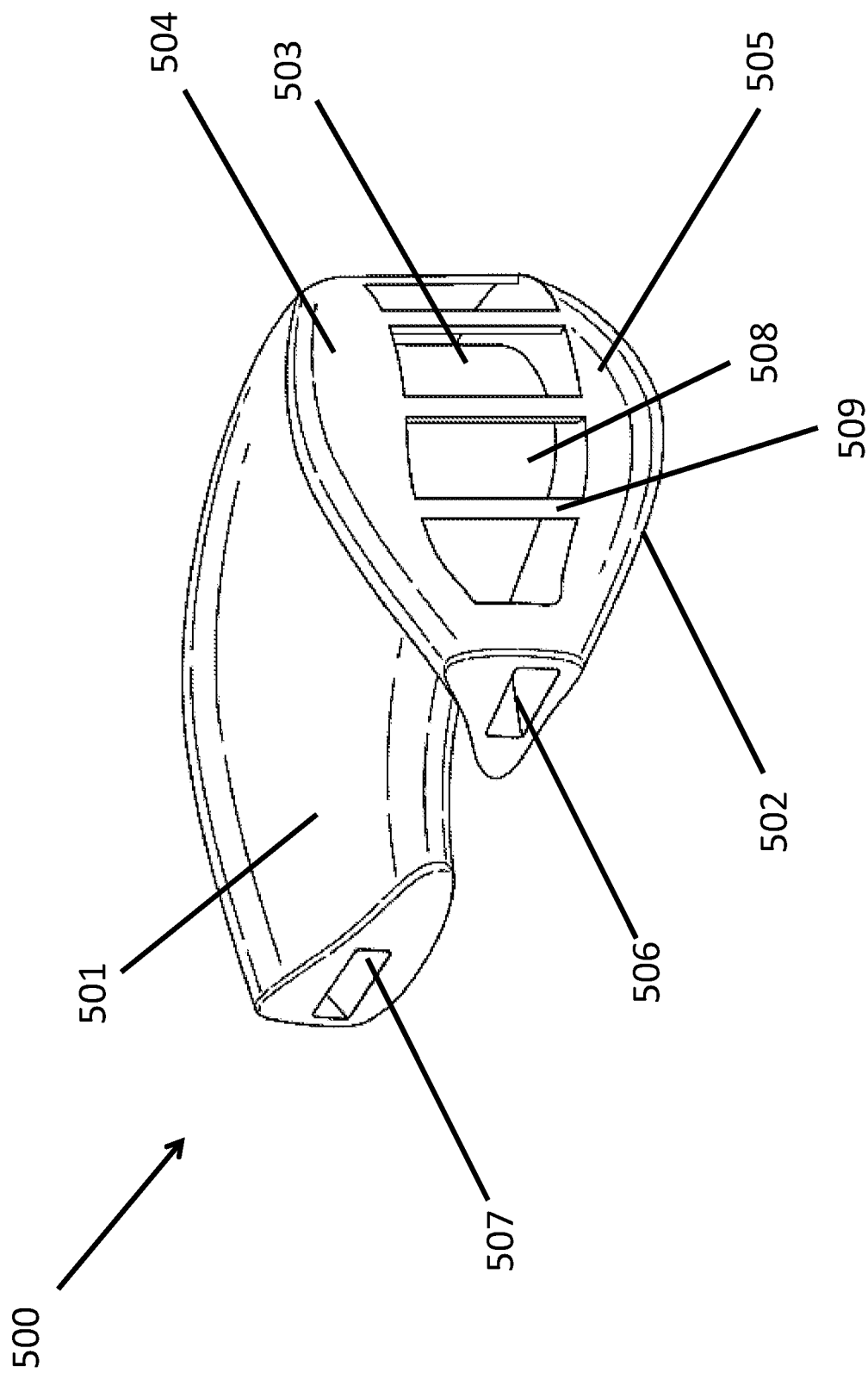
FIG. 5 is another diagrammatic view of a polymeric body of a composite joint implant illustrating how the peripheral recess can have a plurality of polymeric columns forming a plurality of apertures to restrain a ligature of a composite joint implant.

In reference to FIG. 5, the polymeric body (500) can also be comprised of a plurality of apertures (508) or openings that resist circumferential extrusion of the ligature. The plurality of apertures (508) connect the top surface (501) and bottom surface (502) of the polymeric body (500). In some embodiments, at least some of the plurality of apertures (508) display an aspect ratio (height/width ratio) of greater than 1 wherein the height of the aperture is greater than the width of the aperture. In other embodiments, at least some of the plurality of apertures (508) display an aspect ratio (height/width ratio) less than 1 wherein the width of the aperture is greater than the height of the aperture. In certain aspects of the invention, the polymeric body (500) can be comprised of a series of apertures (508) with varying aspect ratios greater than 1 and less than 1. Certain designs of the present invention will assist in placement of the ligature in and around the polymeric body (500) while restraining and limiting displacement of the ligature from the polymeric body (500) when placed under a compressive load. The plurality of apertures (508) are separated by a plurality of polymeric columns (509). The polymeric columns (509) may display an aspect ratio greater than 1. The polymeric body (500) can include apertures (508) of varying sizes that surround the periphery. The recess (503) formed by the top lip (504) and the bottom lip (505) end at the posterior opening (506) and anterior opening (507). The posterior opening (506) and anterior opening (507) can have the same or different geometries. Polymeric columns (509) have the same width, and are separated by a distance around the periphery that is the same between each polymeric column.

Figure 6:
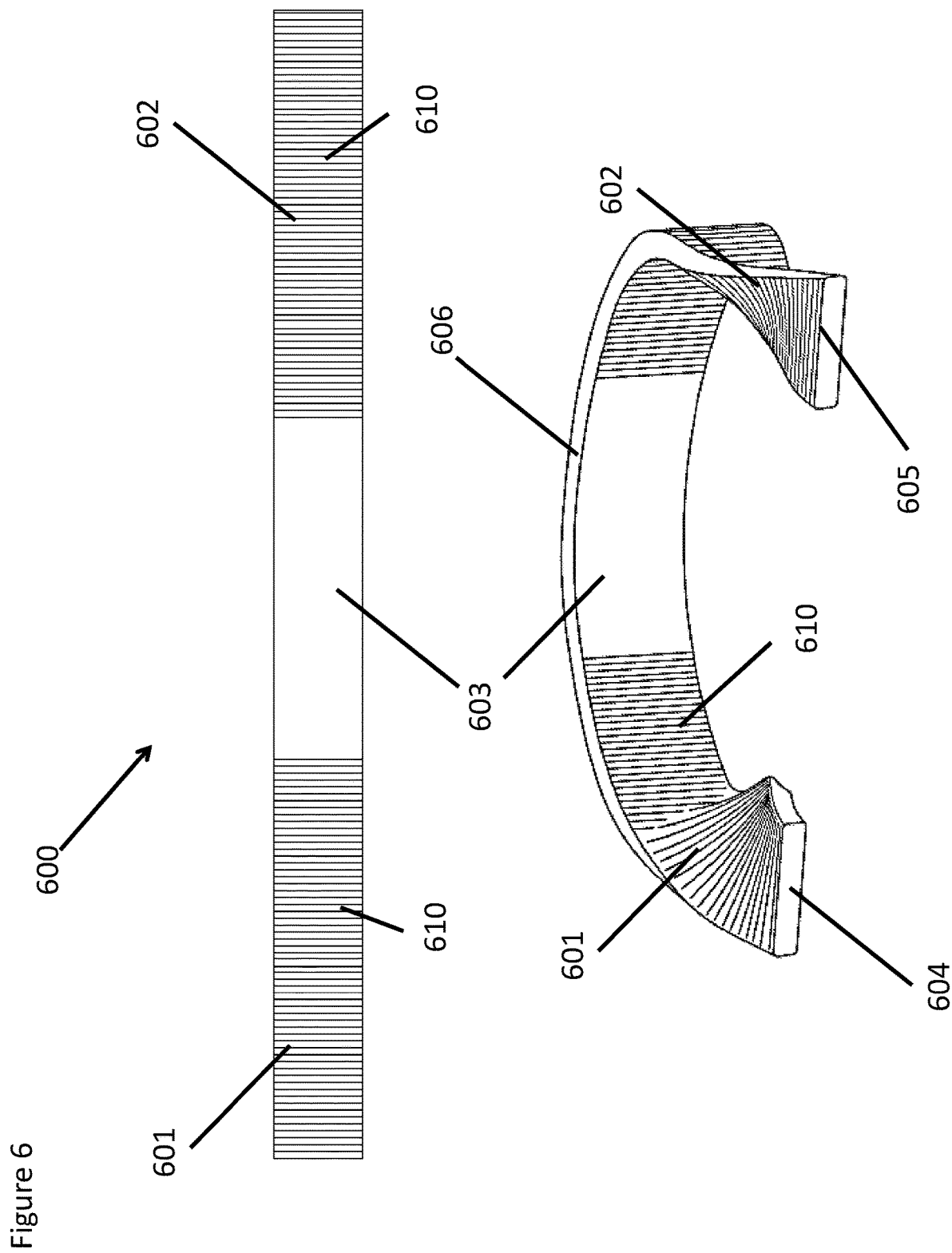
FIG. 6 is a pictorial diagram of a ligature component illustrating how it can change orientation.
Figure 7:
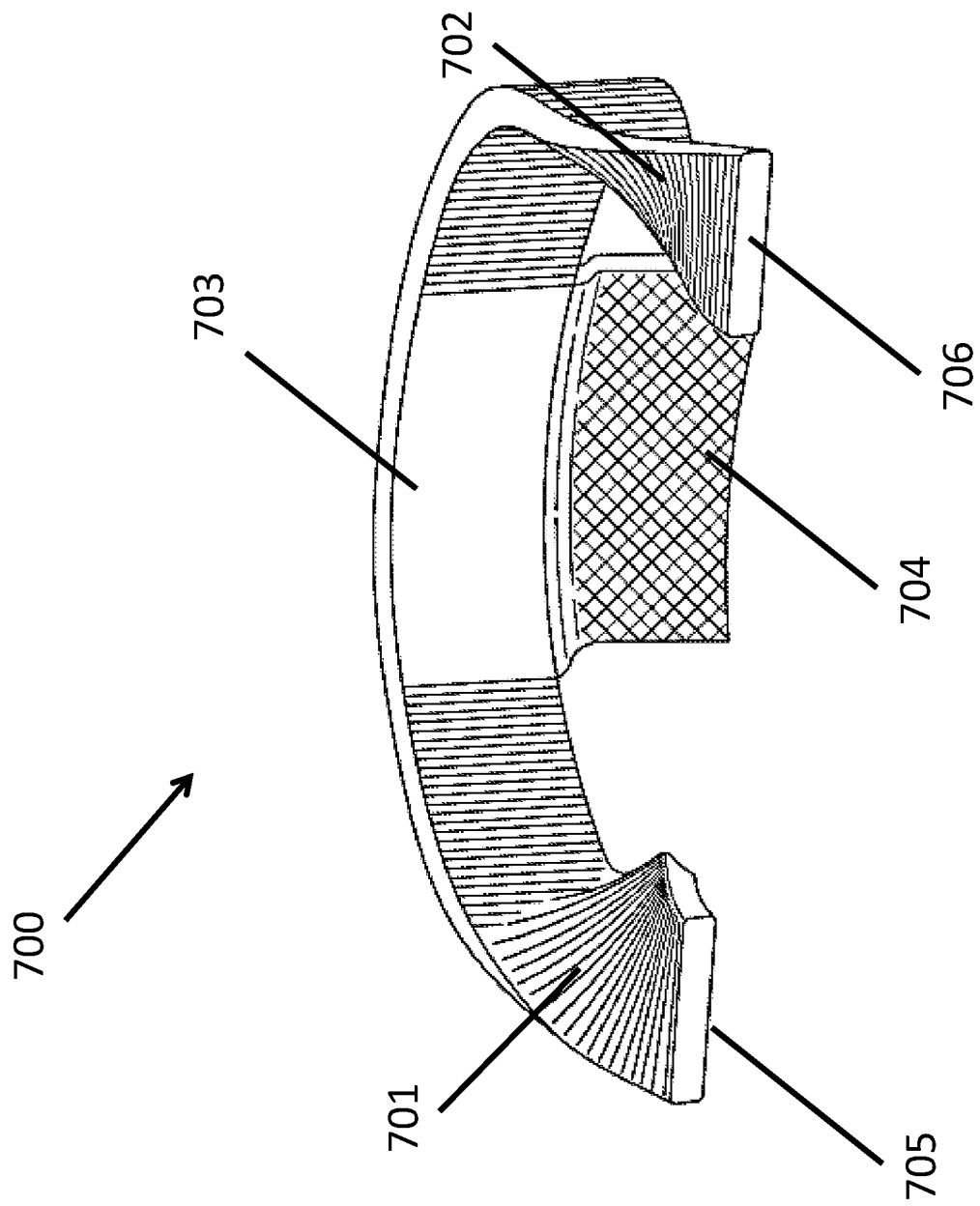
FIG. 7 is a pictorial diagram of a ligature component with a change in orientation along with a peripheral flap.

The composite joint implant is held in place in vivo through the use of the ligature (FIGS. 6-7). The ligature (600) can be comprised of a plurality of fibers and/or yarns. The ligature wraps around the polymeric body, conforming with a central region (603), the anterior end (601) and posterior end (602). The ligature can be compromised of varying cross-sections that provides a resilient and conforming material to support tensile loading of the composite joint implant. The central region of the ligature can be modified with chemistries that support adherence to the polymeric body and/or the encapsulation material. The anterior end (601) and/or the posterior end (602) can be modified with chemistries that support osseointegration in bone. Examples of such chemistries include calcium salts, calcium phosphates, hydroxyapatite, demineralized bone matrix, biomolecules such as type I collagen, mineralizing peptide sequences, hydroxy (—OH) groups among others. The ligature can conform to a range of shapes and rotations based on the means of construction. The central region (603) is further defined by having a thickness (606) which can be similar to or vary from the thickness of the anterior end (604) or the thickness of the posterior end (605). Variation in thickness can ensure a lock-fit placement of the ligature (600) around a designed polymeric body and also assist with placement in the body through the design of material. The anterior end (601) and posterior end (602) can be further defined by a plurality of ridges (610) which can assist with fixation by increasing surface area of the ends of the ligature.

In reference to FIG. 7, the ligature can be further defined by having a central region (703) flanked by a posterior end (701), anterior end (702) and a peripheral flap (704). The peripheral flap (704) is comprised of a conformable surface that can provide additional attachment means of the ligature to the polymeric body or to surrounding tissue structures during in vivo placement. The peripheral flap can be further modified with chemistries for adjoining to the polymeric body, soft tissue, or hard tissue in the body. This modification can include the encapsulation material for integration with the polymeric body. The peripheral flap is attached the central region (703) of the ligature (700) and can extend the entire length of the central region or be preferentially attached to a portion of the central region (703). In some embodiments, the peripheral flap could extend downwards (704), upwards or in both directions of the polymeric body to provide additional attachment as necessary. Posterior end 701 has a thickness (705), which can be the same or different than the thickness (706) of anterior end (702).

In some embodiments, the reinforcing element can be comprised of a first fabric, a second fabric which are connected by a fiber present in both the first fabric and the second fabric. In some embodiments the reinforcing element can be folded so that multiple layers of the first fabric and/or the second fabric can support the polymeric body. In some embodiments the reinforcing element can be heat set to partially form a three-dimensional shape to resemble the shape of the polymeric body. In some embodiments the reinforcing element can be heat set to partially form a three-dimensional shape to resemble the shape of the meniscus. In some embodiments the reinforcing element can provide fixation points around the periphery of the composite joint implant. These fixation points of the reinforcing elements allow the placement of surgical devices used for attachment including suture, staples, tacks, adhesives.

In some embodiments the reinforcing elements are comprised of a first surface, a second surface, and a plurality of fibers that create a cavity between the first and bottom surface. The first fabric is shaped to have a concave surface and the second fabric is shaped to have a convex surface. The cavity provided by the plurality of fibers provides considerable porosity by preferentially separating the first surface from the second surface. This orientation provides a space that can have a varying porosity of 10-95% and more preferably 40-80%. By having a high porosity, the cavity can fully be encased in the polymeric body material. In some embodiments of the present invention, it may be applicable to use more than one reinforcing element by direct combination with another reinforcing element. In certain embodiments of the present invention, the first fabric and the second fabric of the reinforcing element do not have to be exactly equidistant nor do they need to be planar but can have varying distance between the fabrics. Additionally, individual fibers from the plurality of fibers that connect the first fabric and the second fabric can be removed to generate regional variations in compressive properties, tensile properties, shapes, and thicknesses. In some embodiments the scaffold mimics the tensile properties of a subject's meniscus. Combination of the scaffold with the polymeric body forms the construct which in some embodiments is able to mimic the tensile and compressive properties of a subject's meniscus. In a preferred embodiment the construct can resemble the function, shape and size of a meniscus.

Figure 8:
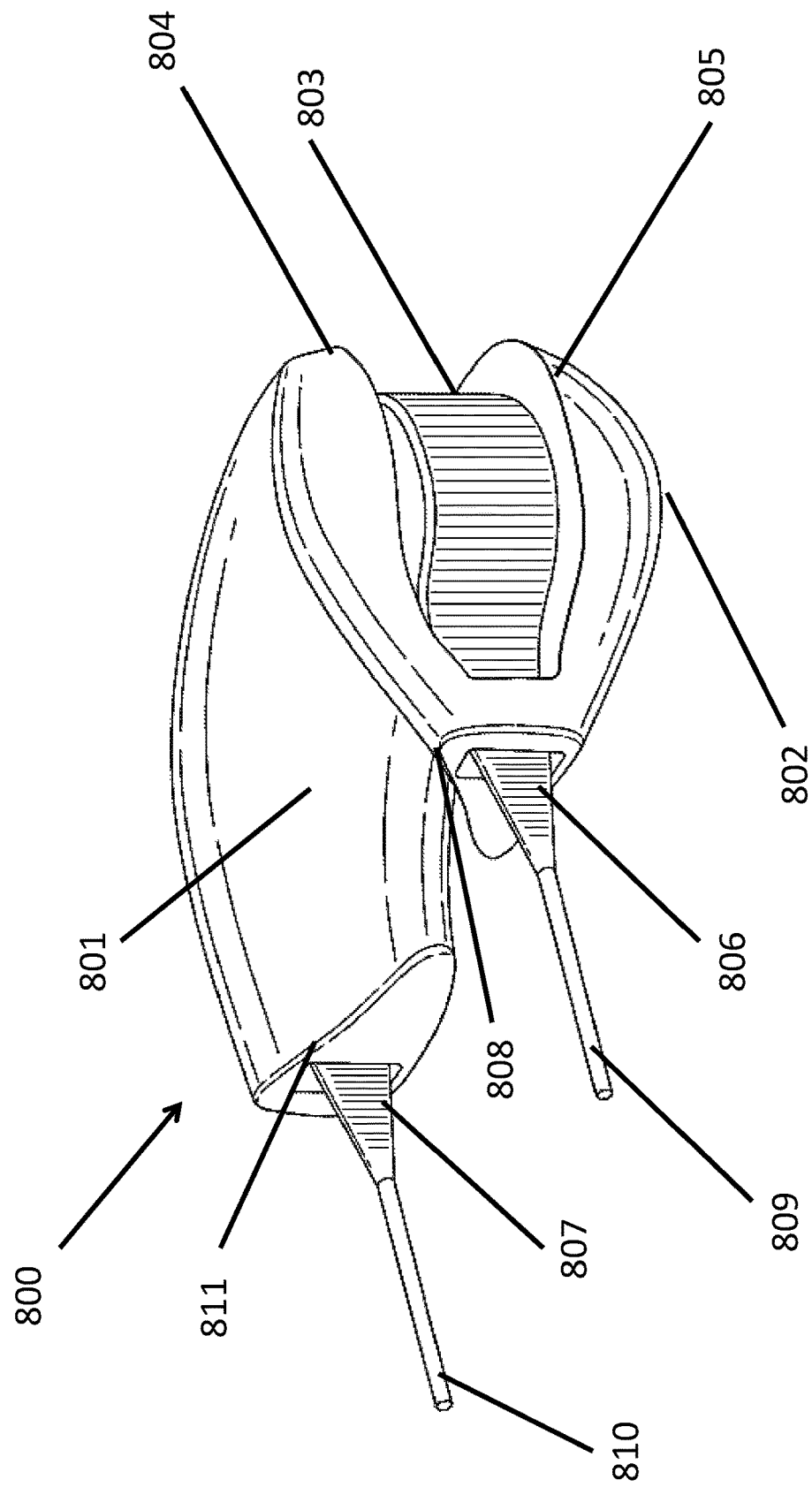
FIG. 8 is a diagrammatic view of a composite joint implant illustrating a mode of the polymeric body, ligature, and reinforcing element.

In reference to FIG. 8, an example of the composite joint implant (800) appears. The composite joint implant (800) is defined by a top surface (801) and a bottom surface (802), a top lip (804), a bottom lip (805), that are separated by a ligature (803) that resides in a recess created between the top lip (804) and the bottom lip (805). The ligature (803) is comprised of a narrowing posterior end (807) and anterior end (806) that tapers and changes cross-section into an anterior attachment point (809) and posterior attachment point (810), respectively. The composite joint implant is comprised of a triangular cross-section wherein the top surface (801) meets the bottom surface (802) to form an internal edge (808) which is opposite from the ligature (803). The composite joint implant (800) is further comprised of an optional lubricious coating (811) on the articulating surfaces meant to provide wear-resistance and provide a lubricious surface where friction is minimal.

Figure 9:
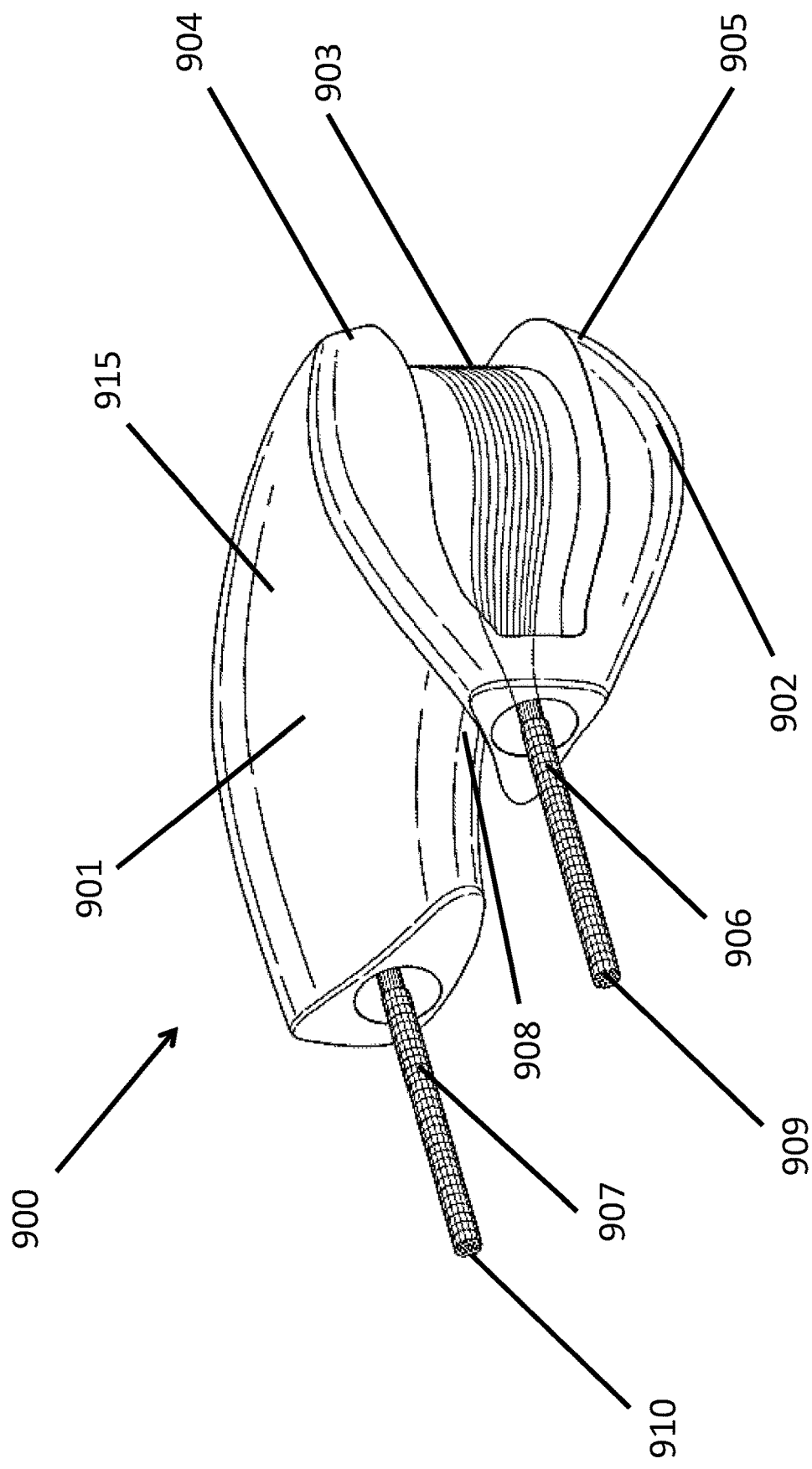
FIG. 9 is another diagrammatic view of a composite joint implant illustrating a different mode of the polymeric body, ligature and reinforcing element.

In reference to FIG. 9, a further example of the composite joint implant (900) is depicted. The composite joint implant (900) is comprised of a ligature (903) wherein the anterior end (906) and posterior end (907) are comprised of bundled fibers that are over-braided into a circular posterior attachment (910) and anterior attachment (909). Top surface (901) meets bottom surface (902) at internal edge (908) of polymeric body (915). Top lip (904) and bottom lip (905) define the periphery of composite joint implant (900), and further define the recess into which ligature (903) has been assembled.

Figure 10:
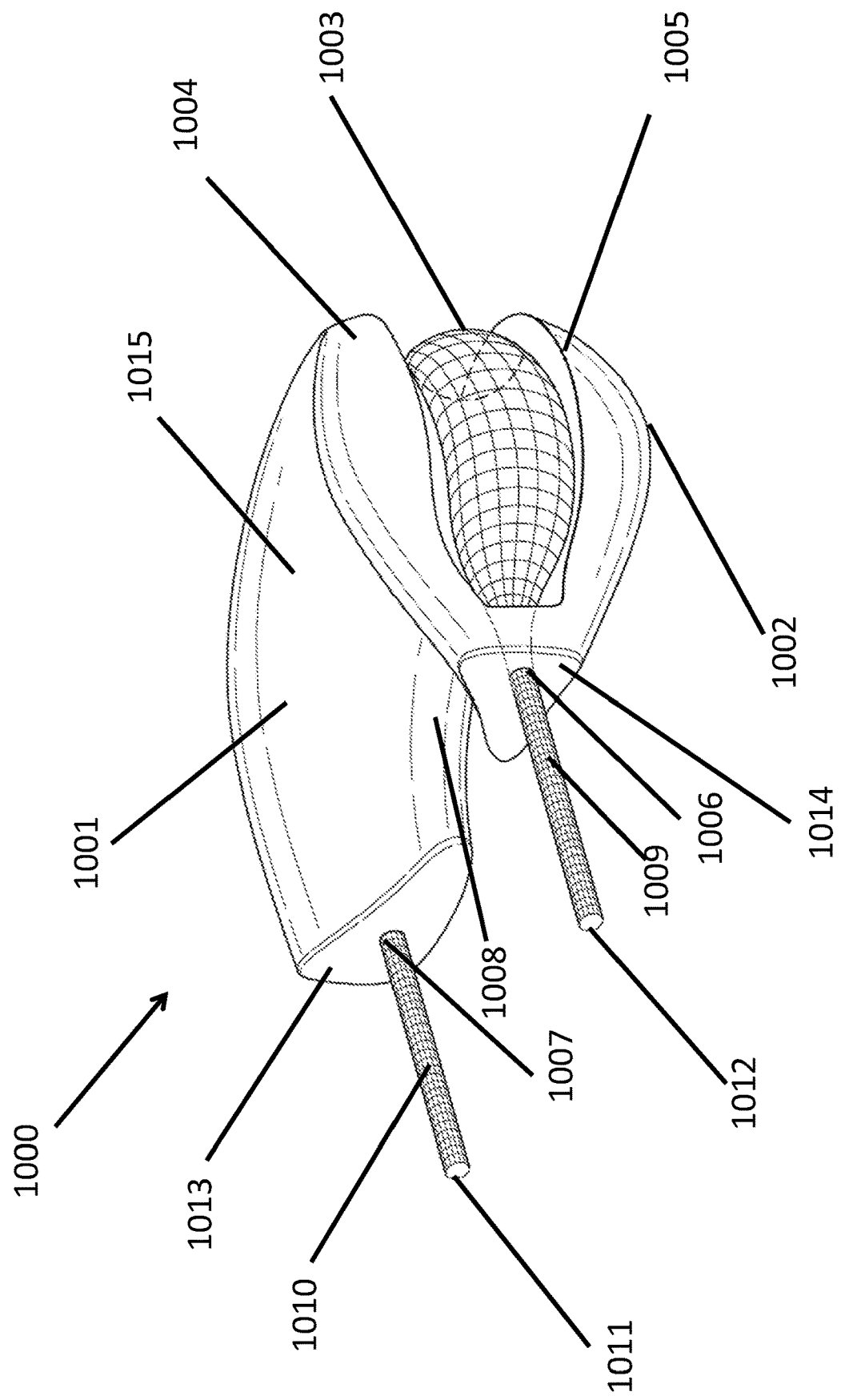
FIG. 10 is a diagrammatic view of a composite joint implant illustrating a different mode of the polymeric body, ligature and reinforcing element.

In a further illustrative example of the invention, FIG. 10, illustrates a composite joint implant (1000) wherein the ligature (1003) exhibits the same structure around the periphery of the polymeric body (1015) and extending out of both the posterior opening (1007) on the posterior face (1013) and the anterior opening (1006) located on the anterior face (1014) of the polymeric body (1015). The same structure extends posteriorly (1010) and anteriorly (1009) for a distance sufficient to enable attachment and terminates into anterior attachment point (1012) and posterior attachment point (1011). Top surface (1001) meets bottom surface (1002) at internal edge (1008) of polymeric body (1015). Top lip (1004) and bottom lip (1005) define the periphery of composite joint implant (1000), and further define the recess into which ligature (1003) has been assembled.

The polymeric body can be reinforced with reinforcing elements (FIG. 11-12) which can be fully incorporated, partially incorporated, or separate from the polymeric body. The reinforcing elements are comprised of fiber or yarn materials that are formed and shaped into three-dimensional structures that can resemble the shape of the polymeric body (FIG. 2-5). The reinforcing elements can be fully incorporated into the polymeric body by formation of the polymeric body into a physical space containing the reinforcing elements. The reinforcing elements can be adjoined to the ligature by any means including but not limited to weft knitting, warp knitting, braiding, weaving, bundling, knotting, looping, among others. The adjoining of the ligature to the reinforcing element creates what is defined as the scaffold. The scaffold can be formed in a singular process or individual processes wherein the ligature and reinforcing elements are formed in separate modes of manufacturing and adjoined or assembled by any means known in the field. In certain embodiments the ligature is formed from higher denier fibers and/or yarns comparative to the reinforcing elements. In certain embodiments the ligature is comprised of a higher areal density compared to the reinforcing elements. In certain embodiments the ligature is comprised of a lower porosity compared to the reinforcing elements. In certain embodiments the reinforcing elements are formed from a different material from the ligature. In certain embodiments the denier for the yarn in the reinforcing elements can range from 10-500 denier. In other embodiments the filament count for multi-filament yarns in the reinforcing elements can vary from 1-96.

In some embodiments the yarn of the reinforcing elements can be loaded with up to 1-30 wt % inorganic particles. In some embodiments the reinforcing elements can wrap around the ligature, preferably around the anterior end and posterior end.

In some embodiments, the scaffold can be comprised of a top surface (1101), a bottom surface (1102), where the two surfaces are separated and connected by a plurality of fibers (1103). The scaffold is comprised of an external edge (1104) where the top surface (1101) and the bottom surface (1102) are not in physical contact. The scaffold is comprised of an internal edge (1105) wherein the top surface is physically connected to but not contacting the bottom surface. The scaffold can resemble the shape and size of a subject's meniscus and is further comprised of a central body (1106), narrowing of the top surface and bottom surface forming a posterior end (1108) and an anterior end (1107). The posterior end and the anterior end have a substantially smaller width and cross-sectional area compared to the central body (1106). The posterior end elongates (1110) and the anterior end elongates (1109) forming the ligature. The posterior end of the ligature includes both the top surface (1101), the bottom surface (1102), and a plurality of fibers (1112) that connect and reinforce the posterior end of the ligature. The anterior end of the ligature includes both the top surface (1101), the bottom surface (1102), and another plurality of fibers (1111) that connect and reinforce the anterior end of the ligature. In some embodiments the posterior end of the ligature and the anterior end of the ligature can possess the same mechanical properties. In some embodiments of the present invention the posterior end of the ligature and the anterior end of the ligature can possess differing mechanical properties. The tip of the posterior end (1114) provides a tab-like structure for attachment to tissue in the subject's body. The tip of the anterior end (1113) provides a second tab-like structure for attachment to tissue in the subject's body for fixation of the composite joint implant.

Figure 12:
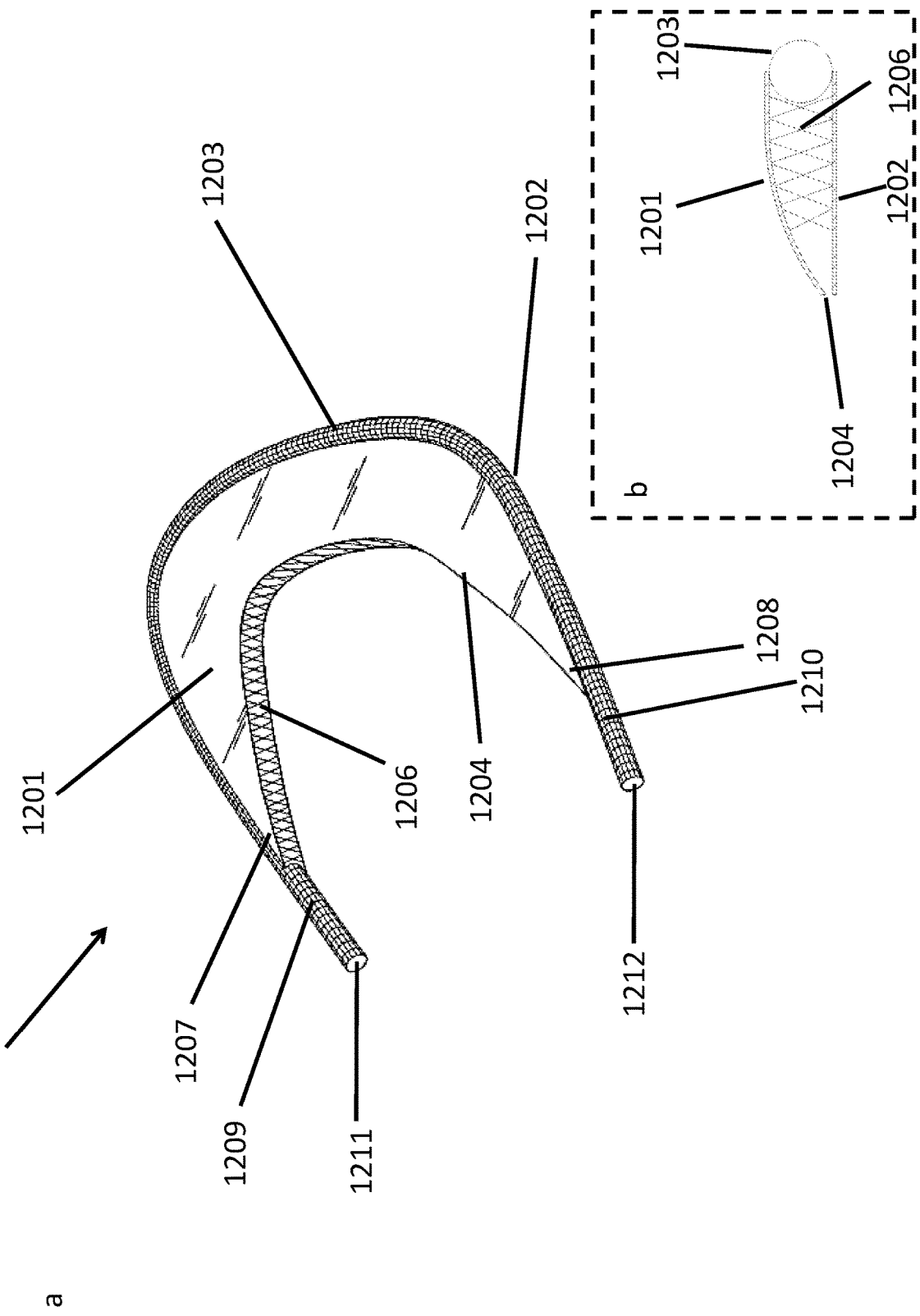

In some embodiments the scaffold can be comprised of a ligature and a reinforcing element formed in separate manufacturing processes (1200). As illustrated in FIG. 12, the scaffold is comprised of a top surface (1201), a bottom surface (1202), a ligature formed in a separate manufacturing process (1203) that surrounds the periphery of the scaffold. The scaffold can be further comprised of an internal edge (1204) wherein the top surface (1201) and the bottom surface (1202) are adjoined but do not contact. The top surface (1201) and the bottom surface (1202) are separated and connected by a plurality of fibers (1206) that can feature varying height from the internal edge (1204) to the ligature (1203). The top surface (1201) and bottom surface (1202) can form a posterior end (1207) and an anterior end (1208) that narrows and connects to the ligature (1203) forming a composite structure. The combinatorial structures extend into ligature posterior end 1209 and ligature anterior end 1210 that terminate into attachment ends 1211 and 1212, respectively. In reference to FIG. 12b, a cross-sectional illustration of the scaffold is displayed identifying the ligature (1203), the top surface (1201), the bottom surface (1202), the internal edge (1204) and the plurality of fibers (1206) that connect and separate the top surface (1201) and the bottom surface (1202).

Figure 13:
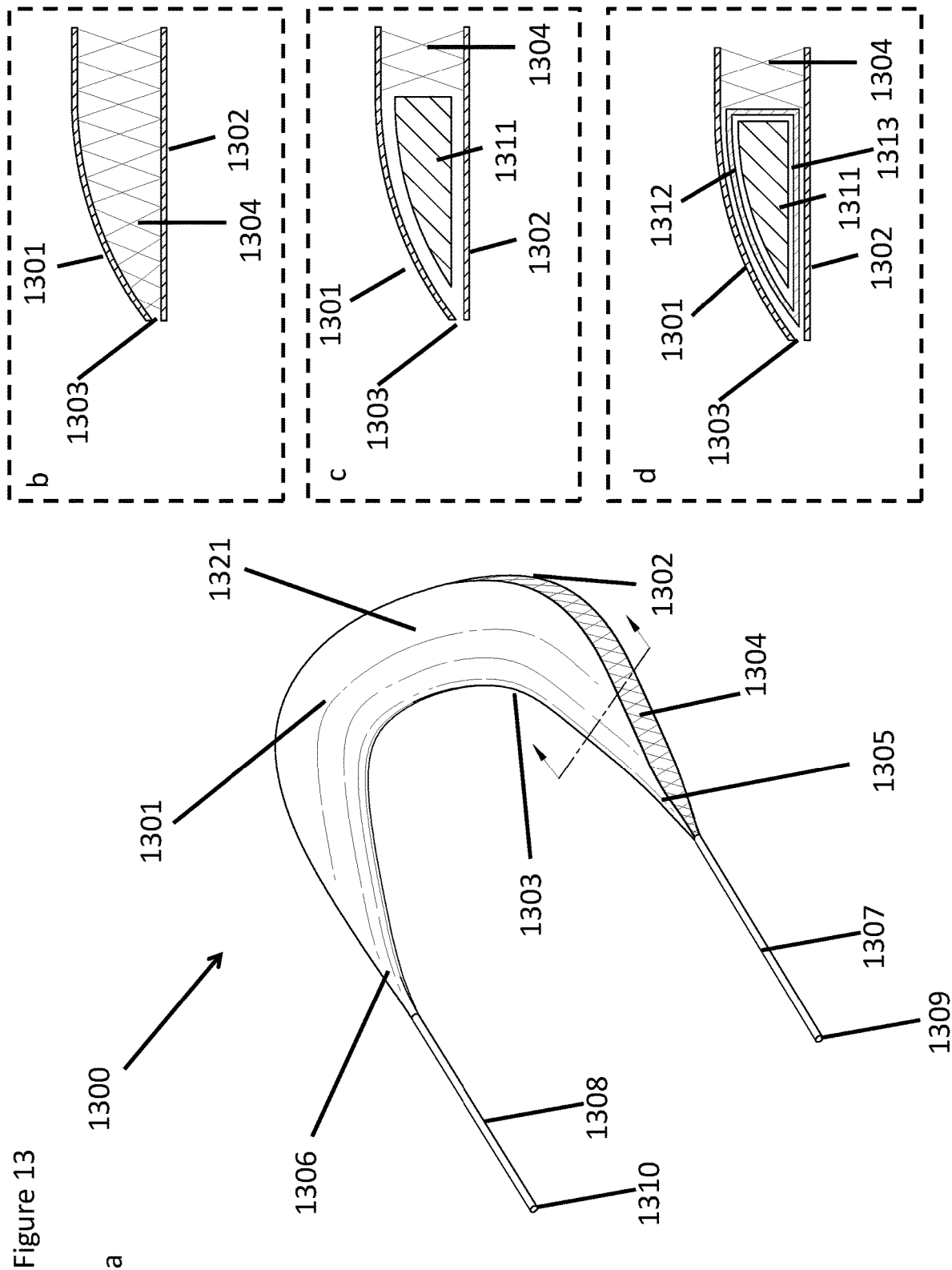

In another embodiment, the scaffold (1300) can be comprised of a top surface (1301), a bottom surface (1302), where the two surfaces are separated and connected by a plurality of fibers (1304). The scaffold is comprised of an external edge where the top surface (1301) and the bottom surface (1302) are not in physical contact. The scaffold is comprised of an internal edge (1303) wherein the top surface is physically connected to the bottom surface. The scaffold can resemble the shape and size of a subject's meniscus and is further comprised of a central body (1321), narrowing of the top surface and bottom surface forming a posterior end (1306) and an anterior end (1305). The posterior end and the anterior end have a substantially smaller width and cross-sectional area compared to the central body (1321). The posterior end elongates (1308) and the anterior end elongates (1307) forming the ligature. The posterior end of the ligature includes both the top surface (1301), the bottom surface (1302), and may include the plurality of fibers (1304) that connect and reinforce the posterior end of the ligature. The anterior end of the ligature includes both the top surface (1301), the bottom surface (1302), and may include a plurality of fibers (1304) that connect and reinforce the anterior end of the ligature. In some embodiments the posterior end of the ligature and the anterior end of the ligature can possess the same mechanical properties. In some embodiments of the present invention the posterior end of the ligature and the anterior end of the ligature can possess differing mechanical properties. The tip of the posterior end (1310) provides a rope-like structure for attachment to tissue in the subject's body. The tip of the anterior end (1309) provides a second rope-like structure for attachment to tissue in the subject's body for fixation of the composite joint implant. Additionally, FIG. 13 illustrates different cross-sectional modes where the scaffold can be combined with the polymeric core (1311). In reference to FIG. 13b the polymeric core is not included in the scaffold (1300). In reference to FIG. 13c, the polymeric core (1311) is fully encapsulated by the top surface (1301), the bottom surface (1302), and is adjacent to the plurality of fibers (1304) as well as the internal edge (1303). In reference to FIG. 13d, the polymeric core (1311) can be further encapsulated by a second top surface (1312) and a second bottom surface (1313) which can assist with retaining the polymeric body with the scaffold. The second top surface (1312) and the second bottom surface (1313) are adjacent to the first top surface (1301), the first bottom surface (1302), the plurality of fibers (1304) and the internal edge (1303). The materials of the second top surface (1312) and the second bottom surface (1313) can be any suitable material, such as, for example, those materials useful for constructing the top surface (1301) and bottom surface (1302). Those surfaces can be made from the same or different materials, or combinations thereof.

Figure 14:
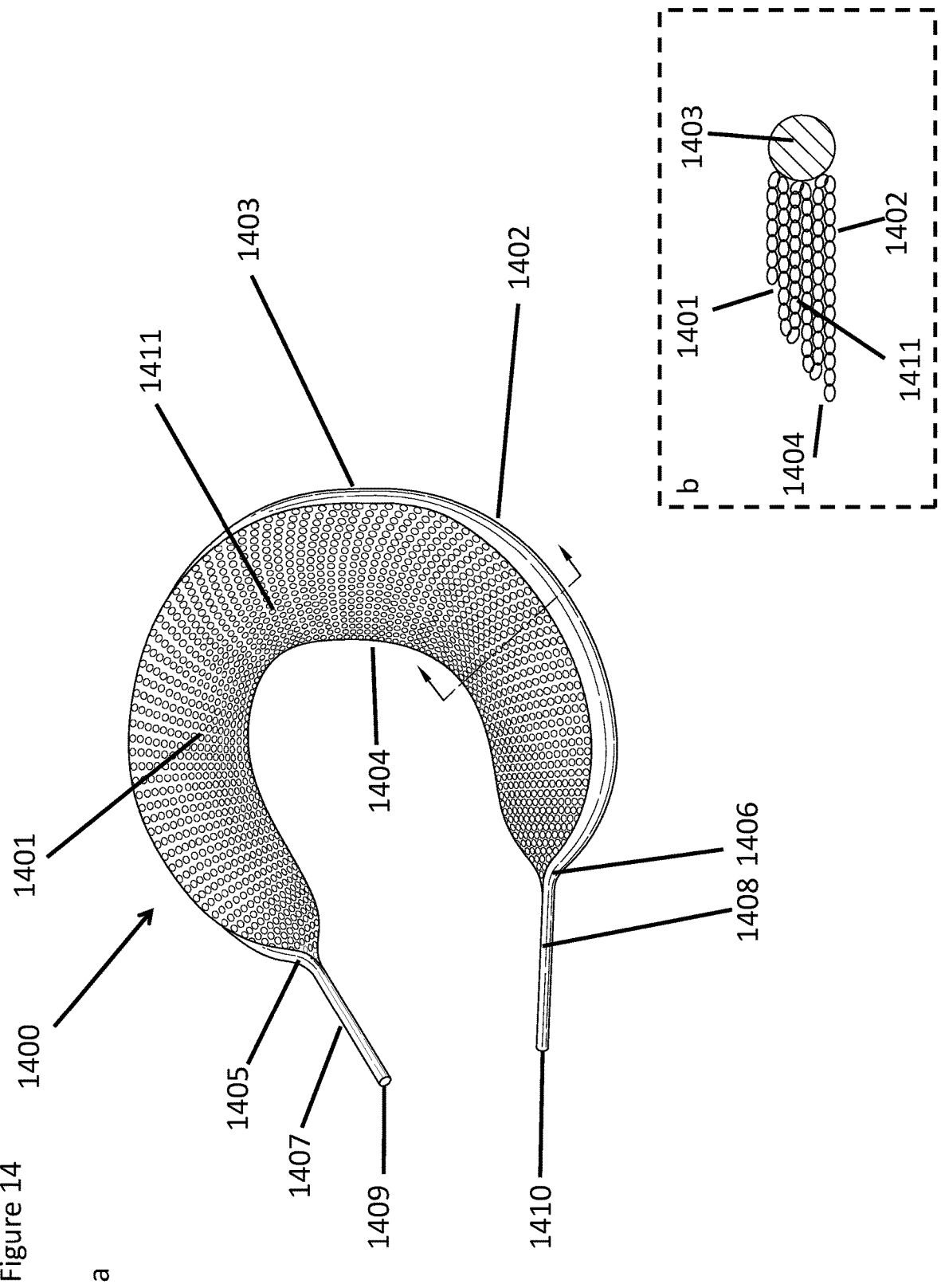

In some embodiments the scaffold (1400) can be comprised of a ligature (1403) and a reinforcing element (1411) formed in a singular manufacturing process. As illustrated in FIG. 14, the scaffold (1400) is comprised a plurality of loops that are formed from a fiber or yarn. The plurality of loops is formed in a manner that a minimal fiber or yarn ends are used and creates a coherent structure. The scaffold (1400) is comprised of a top surface (1401), a bottom surface (1402), a ligature (1403) formed in the same manufacturing process that surrounds the periphery of the scaffold. The scaffold can be further comprised of an internal edge (1404) wherein the top surface (1401) and the bottom surface (1402) are adjoined. The top surface (1401) and the bottom surface (1402) are separated and connected by a plurality of loops that can feature varying height from the internal edge (1404) to the ligature (1403). The top surface (1401) and bottom surface (1402) can form a posterior end (1405) and an anterior end (1406) that narrows and connects to form part of the ligature (1403) forming the scaffold (1400). The posterior end (1407) and anterior end (1406) extend to form an elongated posterior (1407) and anterior (1408) ligature. The respective elongated ends terminate into the posterior end (1409) and the anterior end (1410). The ligature (1403) can be constructed from a differing material compared to the reinforcing element (1411) and display larger cross-sectional area. In some embodiments additional circumferential fibers are present radially between the posterior end and the anterior end of the scaffold providing circumferential reinforcement from the internal edge (1404) to the ligature (1403).

FIG. 15 illustrates the encapsulation material (1509) which completely covers the ligature around the periphery (1503) of the implant strengthening its attachment to the polymeric body, (1515) forming the composite joint implant (1500). Top surface (1501) meets bottom surface (1502) at internal edge (1508) of polymeric body (1515). Anterior opening (1504) and posterior opening (1505) allow anterior end (1506) and posterior end (1507) of the ligature to emerge from polymeric body (l515).

Implantation and fixation of the composite joint implant into a subject can use any means available and standard practice of care for meniscus surgeries, joint intervention, and arthroscopic techniques. A standard arthroscopic approach is used, for example with anteromedial and anterolateral portals plus a posteromedial or posterolateral portal depending on whether a medial or lateral meniscal replacement is to be performed. The anterior and posterior horns of the meniscus are then transected, and the entire meniscus is removed. Using a drill guide, two trans-osseous tunnels are drilled into the tibia, at the locations of the anterior and posterior meniscal roots. In reference to FIG. 16, the composite joint implant (1601) can then be passed into the joint via an enlarged arthroscopy portal on the appropriate side of the knee (medial or lateral) and the anterior end (1602) and posterior end (1603) of the ligature passed through the anterior (1604) and posterior (1605) tibial tunnels respectively. Either the posterior end (1603) or the anterior end (1602) of the ligature passing through the tunnel is pulled to tension the implant. An interference screw or similar fixation is then placed and used to secure either the anterior end (1606) or the posterior end (1607) of the ligature first. Second, the opposite end of the ligature in the other trans-osseous tunnel is then tensioned and an interference screw fixation or similar fixation is used to fix it in place. The joint capsule, the fascias and skin are then sutured and closed. The ligature elements running into the bone tunnels will over time further adhere to the bone, having been coated in osteogenic materials such as hydroxyapatite or similar. Aside from an interference screw, other fixation tools suitable to secure the ligature to the bone can be utilized such as suspensory fixations such as an fasteners, spiked washers, or staples, or combinations thereof.

In reference to FIG. 17, additional types of fixation beyond transosseos means for the composite joint implant (1701) can also be employed by means of a peripheral flap (1705). The ligature may have a wider central region (1702)

that is flanked by posterior end (1703) and an anterior end (1704). The central region (1702) can feature a peripheral flap (1705) that extends beyond the body of the composite joint implant (1701) and allows attachment to tissue structures within the subject. Examples of attachment of the peripheral flap (1705) include the joint capsule or surrounding soft tissue using sutures or biological glues. This peripheral fixation would be in addition and optional to the trans-osseous tunnel fixations described above in FIG. 16.

As an illustrative example for the composite joint implant, a manufacturing methodology is presented in FIG. 18 and FIG. 19. FIG. 18 shows expanded manufacturing path wherein the ligature and the reinforcing element are formed in separate processes. FIG. 18 demonstrates the formation of ligature (1801) and reinforcing element (1802) occur in parallel fashion. These two elements are combined to form a scaffold (1803). The scaffold can be chemically treated (1805) prior to joining with the polymeric body formed separately (1804). The combination of the scaffold and polymeric body forms the construct (1806) which can then be coated with an encapsulation material (1807) forming the composite joint implant. The implant is cleaned (1808) where it can be further dehydrated (1809) or hydrated (1810) dependent on the chemistry. The implant is then packaged (1811), terminally sterilized using any known method in the field including but not limited to ethylene oxide, peracetic acid, irradiation, dry heat, nitrogen dioxide amongst others (1812). The implant is then ready for use and is placed in a subject for meniscus replacement and/or repair (1813). In FIG. 19, the ligature and the reinforcing element are formed in a singular process forming the scaffold and forgoes the additional steps of creating these structures individually (1901). The scaffold can be chemically treated (1902) to assist with integration during construct formation (1903). The implant can be cleaned, removing unwanted materials (1904), and dependent on the chemistry hydrated (1906) or dehydrated (1905). The implant is then packaged (1907), sterilized using any known methods in the field including but not limited to ethylene oxide, irradiation, peracetic acid, dry heat, nitrogen dioxide amongst others. The sterilized implant can then be implanted into a subject (1909) for meniscus repair and replacement. Additionally, the construct is produced in a single manufacturing process wherein the scaffold is fully encapsulated in the polymer in the same manufacturing process step. The scaffold is held in place during manufacturing by protruding pins or by any other established manufacturing means.

To further illustrate the concepts of the present invention, specific examples were created to embody the varying elements of the composite joint implant. These examples are provided to demonstrate useful implementation of the concepts presented herein and by no means are meant to limit the innovative concepts and methodologies presented.

Example 1

Preparation of Multifilament Yarn and Fiber

Fiber and yarn materials were prepared by melt extrusion and reorientation during a multi-stage drawing using a series of heated Godets. High tenacity poly(ester terephthalate) (HT-PET), ultra-high molecular weight polyethylene (UHMWPE), and polypropylene (PP) monofilament were prepared into monofilament fiber and multi-filament yarn through single or multiple hole spinnerets.

Example 2

Polymeric Body

A polymeric body was shaped and formed into a crescent shaped, semicircular geometry with a trapezoidal, wedge shaped cross section, resembling as closely as possible the anatomical shape of the human natural meniscus, whether the medial or the lateral. The polymeric body features a concave top surface, convex or flat bottom surface. The polymeric body features an internal edge where bottom and top surfaces meet and expand away from each other increasing the thickness of the implant and forming an external edge of the implant. The side of the external edge may feature a recess, cavity or groove which runs at least partly around the entire outer periphery of the body and spans at least a portion of the thickness of the device. The recess can feature a varying depth into the thickness of the body towards the internal edge. The recess can rotate by over 90 degrees and run on the top or bottom surface as it approaches the internal edge at one or both ends of the device. The recess exists in order to allow placing of ligature (Examples 2-8) around the external edge to support circumferential loading of the implant. The ligature extends out one or both of the two ends of the implant for several lengths as it would be used to attach the implant to the adjacent bone (Examples 2). The polymeric body can be formed from injection molding, casting, machining, assembly, or other forming processes known in the field. In one example the polymeric body can be comprised of poly(alcohol)-type materials that are capable of undergoing crystallization during solidification-melting cycles. In this example injection molding of the poly(carbonate urethane) was performed by a multi-zone extruder with heat settings of 160° C., 170° C., 190° C., 190° C., and 200° C.

Example 3

Preparation of Scaffold 1

Example 2 consisting of the polymeric body and the ligature, reinforcing elements, and scaffold (Examples 3 to 8) can be impregnated using casting, compression molding, solution casting, additive manufacturing or injection molding to fully or partially encapsulate the ligature placed in the external groove of the implant. This can be achieved using injection molding by placing the inlet port for molten polymer around the edge of the polymeric body and encapsulating or coating the textile component. This additional injection molding step would allow Example 2 to be represented in a fully anatomical shape and volume mimicking as close as possible the size and shape of either the medial or the lateral meniscus and also mimic the natural tissue attachment by means of an incorporated ligature. The cavity of the polymeric body can be comprised of a protruding lip on either the top surface, the bottom surface, or both surfaces. The protruding lips of the cavity can be separate or connected by a plurality of apertures and/or openings. The plurality of apertures can be varying size, geometry and density around the perimeter of the insert. Overall the cavity of the polymeric body provides a "lock-and-key" mechanism for the ligature component. The encapsulation process is achieved by injection molding of the polymeric resin, preferably a polycarbonate urethane and performed by a multi-zone extruder with heat settings of 160° C., 170° C., 190° C., 190° C., and 200° C.

Example 4: Preparation of Scaffold 2

Figure 11:
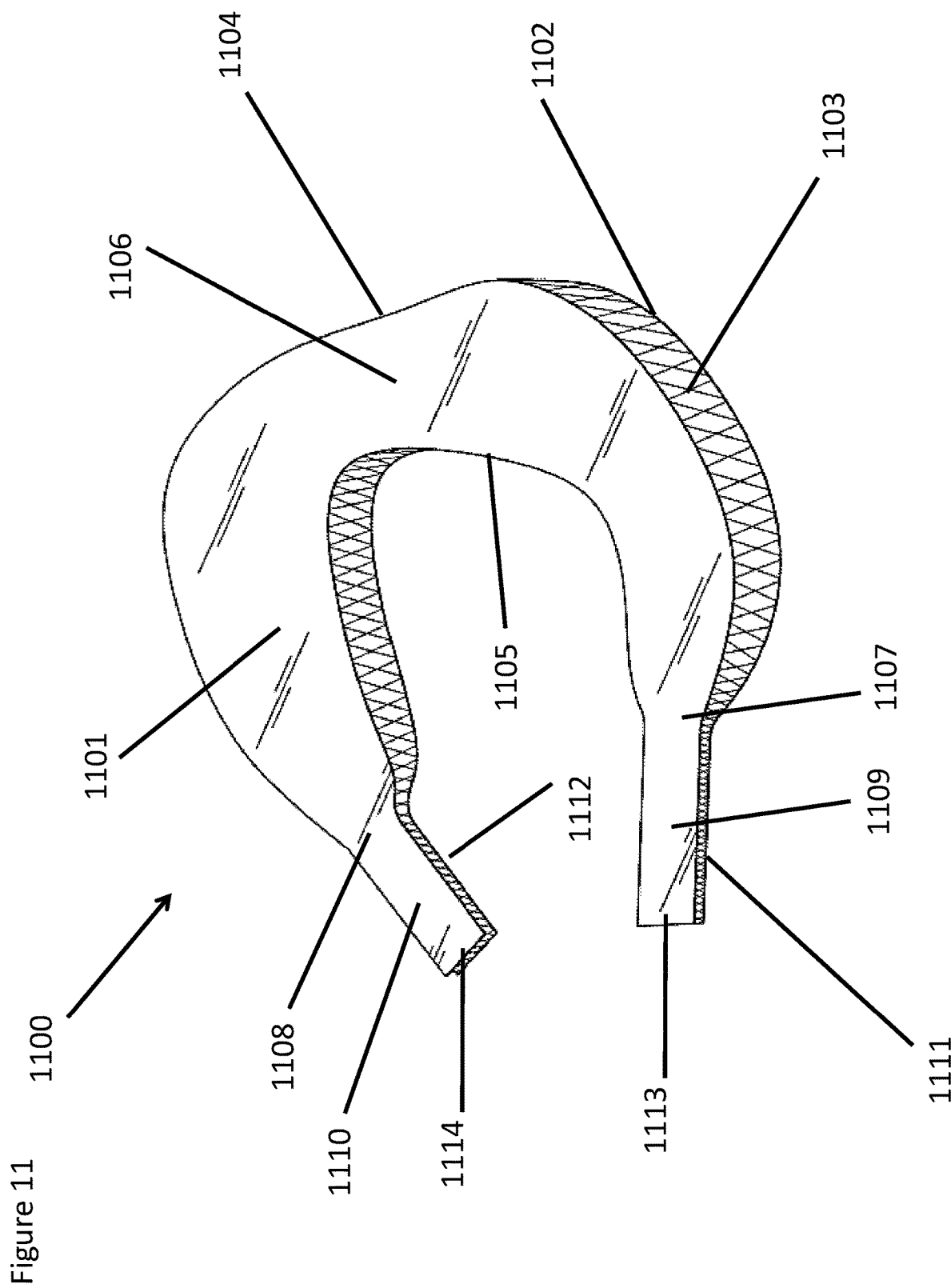
FIG. 11 is a diagrammatic view of a scaffold designed to replicate the size, shape, and mechanics of a meniscus.

A fully threaded two (2) face spacer fabric was produced. The spacer fabric was produced from two (2) fully threaded planar faces using a three (3) yarn system. The faces exhibited a thickness from 0.2-0.5, areal density of 100-400 gsm, and were constructed from 70 denier high tenacity poly(ester terephthalate) (HT-PET) yarn with a tenacity of ≥5 gf/denier and elongation at break of 14%. The spacer element was constructed from 0.2 mm polypropylene (PP) monofilament fiber with a tenacity of ≥3 gf/denier, elongation at break of 20% and separated the formed planar fabrics. A large sheet was knitted (600 mm×600 mm) for further processing. The spacer fabric was cut into an arcuate shape with extensions with a narrowing cross-section as illustrated in FIG. 11. The extensions were compressed and heat set to form a flattened tape. A curved rounded heating element was heated to 150° C. and used to form the internal edge of the implant as well as the varying gradient in z-axis height by partially melting and conforming the PP monofilament. The top planar fabrics were formed into concave surface by the partial melting of the underlying PP monofilament which was incorporated into both planar faces. The arcuate shape was formed from a molding apparatus which was a positive projection of the desired implant shape. The formed implant structure, a scaffold, was placed in a mold and tensioned in place around molding pins. The scaffold was then impregnated and coated with Bionate 80A by a single injection molding step to create a composite joint implant.

Example 5: Ligature 2

A fully threaded two (2) face spacer fabric was produced. The spacer fabric was produced from one (1) fully threaded planar face, one (1) partially threaded planar face, and interconnected by a plurality of spacer elements. The fully threaded planar face exhibited a thickness from 0.2-0.5, areal density of 200-400 gsm, and are constructed from 70 denier high tenacity PET yarn with a tenacity of ≥5 gf/denier and elongation at break of 14%. The partially threaded planar face was able to produce a more porous flat textile structure and exhibited a thickness from 0.2-0.4, areal density of 50-200 gsm, and was constructed from 100 denier high tenacity HT-PET yarn with a tenacity of ≥5 gf/denier. The spacer element was constructed from 0.2 mm HT-PET monofilament fiber and separates the formed planar fabrics by a distance of 1 mm. A large sheet was knitted (500 mm×500 mm) and further processed. The spacer fabric was cut into a strip of thickness 1 mm, width 4 mm, and length 300 mm. The outer 50 mm on either end of the formed strip were compressed and the thickness was minimized to 0.5 mm by heat-setting. The as-formed strap was wrapped around a preformed polymeric core (similar to the polymeric body formed in Example 2) with the fully threaded planar face adjacent to the polymeric core. The combination strip and polymeric core were then over-molded with poly(carbonate urethane). The partially-threaded planar face was wrapped on the external periphery of the polymeric core and allowed a means for molten polymer to over-mold and coat the combination strip and insert complex. After the complex was over-molded the extensions were rotated 90° in orientation and annealed to remain in a 90° rotation by heat setting at 110° C. The rotation allowed for the strip to go from a vertical orientation to horizontal.

Example 6: Ligature 3

A fully threaded two (2) face spacer fabric was produced wherein a stepwise approach was taken wherein a central 4 mm region was fully threaded to include the spacer element and the regions flanking either side were not threaded with the spacer element. The fabric faces was produced from one (1) fully threaded planar face, one (1) partially threaded planar face, and interconnected by a plurality of spacer elements. The fully threaded planar face exhibited a thickness from 0.2-0.5, areal density of 200-400 gsm, and are constructed from 70 denier HT-PET yarn with a tenacity of ≥5 gf/denier and elongation at break of 14%. The partially threaded planar face was able to produce a more porous flat textile structure and exhibited a thickness from 0.2-0.4, areal density of 50-200 gsm, and was constructed from 100 denier HT-PET yarn with a tenacity of ≥5 gf/denier. The spacer element was constructed from 0.2 mm HT-PET monofilament fiber and separates the formed planar fabrics by a distance of 1 mm and spanned a central 4 mm width. The spacer fabric was cut into a strip of thickness 1 mm, width 20 mm (4 mm fully threaded width with 8 mm overlap on either side), and length 300 mm. The planar faces were cut into arcuate crescent shape as outlined in FIG. 12. The design can be modified to afford either a single flap produced from the planar fabrics of the top fabric (on either side of the fully threaded strap in the central region of the textile) or produced from both fabrics to include the partially threaded second fabric face. In this example the flaps from one fabric were used to form an arcuate envelope which formed a pocket and was adjoined to form an internal edge and surround a polymeric core (similar to the polymeric body formed in Example 2). The flaps are foldable, drapable compared to the fully threaded central region. The fabric was arranged so that the flaps were in direct contact with the outer periphery of the polymeric core. The combination strip with flaps and polymeric core were then over-molded with polycarbonate urethane. The partially-threaded planar face was wrapped on the external periphery of the polymeric core and allowed a means for molten polymer to over-mold and coat the combination strip and insert complex. After the complex was over-molded the extensions were rotated 90° and annealed to remain in a 90° rotation.

Example 7: Ligature 4

A fully threaded two (2) face spacer fabric was produced. The spacer fabric was produced from two (2) fully threaded planar faces, and interconnected by a plurality of spacer elements. The fully threaded planar face exhibited a thickness from 0.2-0.5, areal density of 200-400 gsm, and are constructed from 70 denier HT PET yarn with a tenacity of ≥5 gf/denier and elongation at break of 14%. The spacer element was constructed from 0.2 mm HT PET monofilament fiber and separates the formed planar fabrics by a distance of 1 mm. A large sheet was knitted (500 mm×500 mm) and further processed. The spacer fabric was cut into an arcuate shape of thickness 1 mm, width 4 mm, and length 300 mm.

Example 8: Ligature 5

A fully threaded two (2) face spacer fabric was produced with a stepwise gradient in spacer element content. The spacer fabric was produced from two (2) fully threaded planar faces and interconnected by a plurality of spacer elements wherein one-half of the fabric was constructed from a spacer element of HT-PET and the adjacent half was constructed of a spacer element of UHMWPE with a tenacity of ≥28 gf/denier. The fully threaded planar face exhibited a thickness from 0.2-0.5, areal density of 200-400 gsm, and are constructed from 70 denier high tenacity PET yarn with a tenacity of ≥5 gf/denier. The spacer element for both sections (HT-PET and UHMWPE) was constructed from 0.2 mm monofilament fiber and separated the formed planar fabrics by a distance of 1 mm. A large sheet was knitted (200 mm×200 mm) and further processed. The spacer fabric was cut into an arcuate shape of thickness 1 mm, width 4 mm, and length 300 mm. Tab-like projections were created from the half of spacer fabric that contained the UHMWPE spacer element by heat setting and compression.

Example 9: Ligature 6

A ligature was produced by a woven technique. Specifically, a twill weave pattern was constructed from 4 ply 250 denier, 68 filament count high tenacity PET yarn with a tenacity of ≥5 gf/denier and used to construct a 1 mm thick×4 mm wide×300 mm in length. Both ends of the ligature (100 mm) were comprised of a series of alternating ridges. The ridges were created by plying high denier HT PET yarn to create alternating steps in denier weight (i.e. 1000/500). The ridges were formed every 0.5 mm and separated by a pitch of 1 mm. The as-produced woven fabric was heat set at 110° C. under tension for 30 minutes. Ligature was tested for tensile properties. The ends of the ligature were wrapped around 10 mm diameter steel pins and gripped between Instron crosshead clamps. Marks were made across the straps at the inner edge of the clamp jaw to check if any specimen slippage from the clamps occurred. The ligature was then loaded in tension at a rate of 100 mm/min until the ligature broke, with the maximum force recorded. The ligature recorded an ultimate load of 1229+/−231 N with an elongation at break of 10%. The ligature was also tested for cyclic loading and fatigue. The ends of the ligature were wrapped around 10 mm diameter steel pins and gripped between Instron crosshead clamps as described by the ultimate failure load test. Marks were made across the straps at the inner edge of the clamp jaw to check if any specimen slippage from the clamps occurred. After applying 20 preconditioning cycles from 0-50 N, the load was increased to 145 N and 1000 cycles between 70 and 220 N were applied at 1 Hz. This has been previously used to represent the loads experienced by the ligaments (such as the anterior cruciate ligament) during normal walking. Finally, the load was increased to 500N and 2000 cycles between 350 N and 650 N were applied at 1 Hz. This was chosen to double the load range of the first 1000 cycles and be more indicative of loads experienced by the ligaments (such as the anterior cruciate ligament) during jogging. From the elongation data, the resulting strain was calculated at the maximum and minimum load points. All strain values recorded were less than 0.04.

Example 10: Ligature 7

A 500 mm long ligature was produced by a woven technique. Specifically 70 denier high tenacity PET yarn with a tenacity of ≥5 gf/denier was used to construct a 1 mm thick×5 mm wide×50 mm length twill weave at mid-length which is tapered into a circular weave of 4 mm diameter on both ends using tipping. In this example, the circular weave embedded all of the high tenacity PET yarn used in the twill weave construct to maintain high tensile strength throughout. The twill weave mid-section of the ligature is wrapped around the polymeric body cavity, over molded and extended out of one or both ends of the implant in a vertical orientation before tipping. Other variants could include expansion of the circular weave 50 mm from the end back into a 1 mm thick×5 mm wide twill weave for attachment to the bone with interference screws or similar fixation techniques. Other variants could feature a coating which encapsulates or surrounds each individual fibrous element within the engineered bulk of the ligature to provide better adhesion to the polymeric body. This coating is referred to herein as the encapsulation material.

Example 11: Ligature 8

A ligature was produced specifically by braiding high tenacity PET yarn with a tenacity of ≥5 gf/denier to construct a 5 mm diameter×500 mm length braid. Other variants could include longitudinal free-fibers in the mid-section of the ligature which wrap around the polymeric body and are over-braided at exit from the polymeric body on both ends, providing additional strength for attachment to the bone.

Example 12: Formation of Scaffold 3

A scaffold was formed by weft knitting of UHMWPE yarn using forming a three-dimensional weft-knit structure in the likeness of FIG. 14. The structure was formed from on a Shima Sheika knitting machine and was constructed from a plurality of loops forming on top of one another by the interlooping of layers. The scaffold featured a ligature section that was comprised of a dense knit section that exhibited superior tensile properties >900 N in ultimate load. Other variants could feature a combination of yarns and fibers in addition to combination of materials (e.g., UHMWPE with high tenacity PET).

Example 13: Polymeric Body 2

In addition to the features described in Example 2, the ends or horns of the polymeric body could be extended further such that the polymeric body material inserts into the bone tunnel apertures. The ends or horns of the polymeric body can be comprised of poly(alcohol)-type materials that are conforming and flexible. In another example, vertical guide structures could be manufactured into both ends of the polymeric body for reinforcement and ligature placement and positioning. The vertical guide structures could be comprised of poly(alcohol)-type materials with superior compressive modulus and tear strength to the material comprising the rest of the polymeric body.

Example 14: Formation of Composite Joint Implant by Physical Crosslinking Method A composite joint implant was formed by first creating a polymer solution of 10-20% in deionized water that was comprised of 99% poly(vinyl alcohol) (99% hydrolysed) with a molecular weight 89,000-98,000 Da and 1% poly(vinyl pyrrolidone) with a molecular weight of 40,000 Da. The polymer solution was casted around a scaffold and or ligature as described above and underwent numerous freeze-thaw cycles wherein the as-formed implant was frozen to −20° C. at a rate of 2° C./minute. The implant was held at −20° C. for up to 21 hours and then thawed to 20° C. for 3 hrs before undergoing another freezing cycle. This was repeated for numerous cycles with a preferred number of cycles between 3-10. Other variants could feature additional polymers that provide enhanced mechanical and surface properties, for example polyethylene glycol or polyethylene oxide in combination with poly(vinyl alcohol).

Example 15: Formation of Composite Joint Implant by Chemical Crosslinking Method Poly(vinyl alcohol) (PVA) with a molecular weight range of 13,000-23,000 DA (99% hydrolysed) was used without further purification. Glycidyl acrylate, glutaric dialdehyde, and hydrochloric acid were also used without purification. An acrylate modified PVA was synthesized by esterification of pendant alcohol groups on the PVA with glycidyl acrylate in an acidic aqueous environment. A 10-30% PVA solution was prepared by heating the mixture at 80° C. overnight for complete dissolution. An excess of glycidyl acrylate was slowly added, along with HCl to attain a pH of approximately 1.5. The solution was reacted for 24 hrs at 20° C. with constant stirring. Once complete, the acrylated-PVA was precipitated in acetone, filtered, and dried for 12 hours. After acrylation and drying the material was re-dissolved in deionized water at 80° C. at a concentration ranging from 10-20 wt % and was dissolved with the photo-initiator IrgaCure at a concentration of 0.05 wt %. The solution was photopolymerized using UV light source at intensity ranging from 5-30 mW/cm$^2$ for five (5) minutes in a custom mold designed and shaped to match the meniscus of a subject. The mold was pre-loaded with a ligature or scaffold of the above examples so that the ligature or scaffold would be embedded within the polymeric body once formed. Other variants could feature additional polymers that provide enhanced mechanical and surface properties, for example acrylated polyethylene glycol, acrylated polyethylene oxide in combination with acrylated poly(vinyl alcohol).

Example 16: Implantation of Composite Joint Implant

The implant is implanted using a surgical procedure where the natural meniscus, is excised from the joint via a small incision on the knee joint in order to gain access to the articular capsule. The natural meniscus can be removed using an arthroscopic procedure or other cutting technique. Once the natural meniscus has been removed, using the same incision or different incisions, two transosseous tunnels are drilled in the tibial plateau at an angle, similarly to when an antero-cruciate ligament reconstruction is performed. The tunnels may be drilled all the way through the bone featuring a tunnel running all the way through to the opposing surface of the bone, or they may form a socket in the surface of the bone, preferably sited at the anatomic attachment area of the natural meniscus insertional ligaments. The implant, Example 2, can then be placed in between the femoral condyle and tibial plateau where the natural meniscus had been present. Both the anterior and posterior tape like structures (Example 3-8) extending from the implant are directed inwards and into the two transosseous tibial tunnels. Using a force or other surgical instrument the tape like structures (Example 3 to 8) are pulled through the tunnels, tensioning the tape like structure and correctly positioning the implant in a snug manner between the condyles and towards the center of the tibial plateau. Using interference screws or similar devices familiar to arthroscopic surgeons, the tape like structure is fixed in place, thereby fixing the implant on the tibial plateau, thus limiting lateral displacement and implant extrusion.

EMBODIMENTS

Embodiment 1

A composite joint implant for the replacement or repair of meniscus tissue comprising:
a polymeric body comprising a top surface for articulating against a femoral condyle and a bottom surface for bearing against a tibial plateau; and
a ligature comprising a central region disposed in the polymeric body, the central body joining an anterior end and a posterior end.

Embodiment 2

The composite joint implant of embodiment 1, wherein the polymeric body further comprises an anterior opening through which the anterior end of the ligature passes, and a posterior opening through which the posterior end of the ligature passes.

Embodiment 3

The composite joint implant of any one of embodiments 1-2, wherein the polymeric body comprises a recess, and the central region of the ligature is disposed in the recess.

Embodiment 4

The composite joint implant of any one of embodiments 1-3, wherein the top surface joins the bottom surface at an interior edge.

Embodiment 5

The composite joint implant of any one of embodiments 1-4, wherein the top surface terminates in a top lip, and the bottom surface terminates in a bottom lip.

Embodiment 6

The composite joint implant of any one of embodiments 1-5, wherein the top surface and the bottom surface define a periphery.

Embodiment 7

The composite joint implant of any one of embodiments 1-6, wherein the top surface, bottom surface, or both, comprise a lubricious coating.

Embodiment 8

The composite joint implant of any one of embodiments 6-7, wherein the central region of the ligature reinforces the periphery.

Embodiment 9

The composite joint implant of any one of embodiments 1-8, wherein the anterior end of the ligature is adapted to pass through a first transosseous tunnel and attach to a subject.

Embodiment 10

The composite joint implant of any one of embodiments 1-9, wherein the posterior end of the ligature is adapted to pass through a second transosseous tunnel and attach to a subject.

Embodiment 11

The composite joint implant of any one of embodiments 1-10, wherein the ligature comprises a tensile load bearing element that reinforces the polymeric body.

Embodiment 12

The composite joint implant of embodiment 11, wherein the tensile load bearing element comprises fiber, yarn, or a combination thereof.

Embodiment 13

The composite joint implant of any one of embodiments 1-12, wherein the ligature is formed by weft knitting, warp knitting, braiding, weaving, bundling, knotting, looping, and combinations thereof.

Embodiment 14

The composite joint implant of any one of embodiments 1-13, having an anatomical meniscus shape.

Embodiment 15

The composite joint implant of any one of embodiments 1-14, further comprising a reinforcing element that adjoins the ligature to form a scaffold.

Embodiment 16

The composite joint implant of any one of embodiments 1-15, wherein the polymeric body comprises a plurality of apertures separated by a plurality of polymeric columns that restrain the ligature around a periphery of the polymeric body.

Embodiment 17

The composite joint implant of embodiment 16, wherein each polymeric column in the plurality of polymeric columns has the same width.

Embodiment 18

The composite joint implant of any one of embodiments 16-17, wherein each polymeric column in the plurality of columns is separated by a distance that is the same between each polymeric column.

Embodiment 19

The composite joint implant of any one of embodiments 15-18, wherein the ligature, the reinforcing elements, or both, are formed by a plurality of fibers.

Embodiment 20

The composite joint implant according to any one of embodiments 15-19, wherein the ligature and the reinforcing element comprise one or more polymers chosen from polyesters, polyolefins, perhalogenated polyolefins, polyether ether ketones, polyurethanes, polyamides, silicones, nylons, and combinations of two or more thereof.

Embodiment 21

The composite joint implant of any one of embodiments 1-20, wherein the ligature comprises a mono-filament yarn, a multi-filament yarn, or a combination thereof.

Embodiment 22

The composite joint implant of any one of embodiments 15-21, wherein the reinforcing element comprises a mono-filament yarn, a multi-filament yarn, or a combination thereof.

Embodiment 23

The composite joint implant of any one of embodiments 1-22 wherein the polymeric body comprises a polycarbonate urethane, a polyvinyl alcohol, a polyethylene glycol, or a combination thereof.

Embodiment 24

The composite joint implant of any one of embodiments 1-23, wherein the ligature comprises two materials having different melting points.

Embodiment 25

The composite joint implant of embodiment 24, wherein the two materials are present as a major component making more than fifty percent of the ligature by mass and a minor component making less than fifty percent of the ligature by mass.

Embodiment 26

The composite joint implant of embodiment 25, wherein the major component comprises high tenacity poly(ester terephthalate) and the minor component comprises ultra-high molecular weight poly(ethylene).

Embodiment 27

The composite joint implant of any one of embodiments 1-26 wherein the ligature contains at least one fixation mechanism.

Embodiment 28

The composite joint implant of embodiment 27, wherein the at least one fixation mechanism comprises a ladder-rung type structure at the anterior end, at the posterior end, or at both, to allow for attachment to bone.

Embodiment 29

The composite joint implant of any one of embodiments 1-28, wherein the encapsulation material comprises a polycarbonate urethane, a polyvinyl alcohol, polyethylene glycol or a combination thereof.

Embodiment 30

The composite joint implant of any one of embodiments 1-29, wherein the ligature further comprises a peripheral flap for peripheral fixation to at least one tissue in a subject.

Embodiment 31

The composite joint implant of any one of embodiments 1-30, wherein the ligature is formed from a multi-filament yarn of high tenacity polyester having a denier ranging from about 20 to about 2000 denier with a filament count ranging from about 18 to about 96 per yarn.

Embodiment 32

The composite joint implant of any one of embodiments 1-31, wherein the ligature is formed from a multi-filament yarn of ultra-high molecular weight polyethylene having a denier ranging from about 20 to about 900 denier with a filament count ranging from about 18 to about 96 per yarn.

Embodiment 33

The composite joint implant of any one of embodiments 1-32, wherein the ligature is formed from a combination of multi-filament yarn of high tenacity polyester and ultra-high molecular weight polyethylene each having a denier ranging from about 20 to about 900 denier with a filament count ranging from about 18 to about 96 per yarn.

Embodiment 34

The composite joint implant of any one of embodiments 1-33, exhibiting a compressive stiffness ranging from about 0.01 MPa to about 5 MPa along the vertical axis.

Embodiment 35

The composite joint implant of any one of embodiments 1-34, wherein the ligature exhibits a tensile strength from about 150 MPa to about 400 MPa in the long axis of the ligature.

Embodiment 36

The composite joint implant of any one of embodiments 1-35, wherein the composite joint implant is adapted to replace meniscus tissue.

Embodiment 37

A composite joint implant, comprising:
a polymeric body comprising a top surface and a bottom surface that together define a recess,
a ligature comprising a central region joining an anterior end to a posterior end, the central region disposed in the recess,
a reinforcing element comprising a plurality of fibers between the top surface and the bottom surface,
and an lubricious coating that covers at least a portion of the top surface, the bottom surface, or both, of the polymeric body.

Embodiment 38

A scaffold for the repair or replacement of meniscus tissue in a human or animal subject in need thereof, comprising:
a ligature comprising a central region joining an anterior end with a posterior end; and
a reinforcing element providing radial support to the polymeric body.

Embodiment 39

The scaffold of embodiment 38, further comprising a polymeric core encompassed within the scaffold.

Embodiment 40

The scaffold of any one of embodiments 38-39, wherein the ligature contains at least one fixation mechanism.

Embodiment 41

The scaffold of embodiment 40, wherein the at least one fixation mechanism comprises a ladder-rung type structure at the anterior end, at the posterior end, or at both, to allow for attachment to bone.

Embodiment 42

The scaffold of any one of embodiments 38-41, comprising a plurality of fibers.

Embodiment 43

The scaffold of any one of embodiments 38-42, comprising one or more polymers chosen from polyesters, polyolefins, perhalogenated polyolefins, polyether ether ketones, polyurethanes, polyamides, silicones, nylons, and combinations of two or more thereof.

Embodiment 44

The scaffold of any one of embodiments 38-43, comprising a mono-filament yarn, a multi-filament yarn, or a combination thereof.

Embodiment 45

The scaffold of any one of embodiments 38-44, comprising two materials having different melting points.

Embodiment 46

The scaffold of embodiment 45, wherein the two materials are present as a major component making more than fifty percent of the scaffold by mass and a minor component making less than fifty percent of the scaffold by mass.

Embodiment 47

The scaffold of embodiment 46, wherein the major component comprises high tenacity poly(ester terephthalate) and the minor component comprises ultra-high molecular weight poly(ethylene).

Embodiment 48

The scaffold of any one of embodiments 38-47, adapted to be used in the composite joint implant of any one of embodiments 1-37.

Embodiment 49

A method of repairing or replacing meniscus tissue in a human or animal subject in need thereof, comprising:

implanting into the subject a composite joint implant comprising
a polymeric body comprising a top surface and a bottom surface,
a ligature comprising a central region joining an anterior end to a posterior end, the central region disposed between the top surface and the bottom surface,
a reinforcing element embedded in the polymeric body comprising a plurality of fibers connecting the top surface to the bottom surface.

Embodiment 50

The method of embodiment 49, wherein the top surface and the bottom surface define a recess, and the ligature is disposed within the recess.

Embodiment 51

The method of any one of embodiments 49-50, wherein the ligature is embedded in the polymeric body.

Embodiment 52

The method of embodiment 51, wherein the polymeric body comprises poly(vinyl alcohol).

Embodiment 53

The method of any one of embodiments 51-52, wherein the polymeric body comprises at least one poly(carbonate urethane).

Embodiment 54

The method of any one of embodiments 49-53, wherein the composite joint implant is the composite joint implant of any one of embodiments 1-37.

Embodiment 55

A method of making a composite joint implant, comprising:
combining a ligature, which comprises a central region joining an anterior end to a posterior end, with
a polymeric body comprising a recess for encompassing the ligature.

Embodiment 56

A method of making a composite joint implant, comprising:
combining a ligature, which comprises a central region joining an anterior end to a posterior end, with
a polymeric body by polymerizing the polymeric body in a mold comprising the ligature.

Embodiment 57

The method of any one of embodiments 55-56, wherein the composite joint implant is the composite joint implant of any one of embodiments 1-37.

Embodiment 58

A method of making a scaffold, comprising:
forming a reinforcing element with a ligature.

Embodiment 59

The method of embodiment 58, wherein the scaffold is the scaffold of any one of embodiments 38-48.

INDUSTRIAL APPLICABILITY

Certain embodiments of the present invention are suitable for manufacture on an industrial scale.

What is claimed is:

1. A composite meniscus implant for the replacement or repair of meniscus tissue comprising:
a polymeric body comprising a top surface for articulating against a femoral condyle and a bottom surface for bearing against a tibial plateau, the top surface joining the bottom surface at an interior edge and joining the bottom surface at a periphery opposite the interior edge to form an anatomical meniscus shape;
a ligature comprising a central region disposed in the polymeric body, an anterior end, and a posterior end, the central region joining the anterior end and the posterior end; and
a reinforcing element that adjoins the ligature to form a scaffold,
wherein the polymeric body comprises a recess along the periphery, and the central region of the ligature is disposed in the recess,
wherein the top surface of the polymeric body terminates in a top lip, and the bottom surface of the polymeric body terminates in a bottom lip,
wherein the periphery of the polymeric body comprises a plurality of apertures separated by a plurality of polymeric columns, wherein the plurality of polymeric columns extend from the top lip of the polymeric body to the bottom lip of the polymeric body,
wherein the ligature is restrained around the periphery of the polymeric body between the recess and the plurality of polymeric columns,
wherein the polymeric body further comprises an anterior opening through which the anterior end of the ligature passes, and a posterior opening through which the posterior end of the ligature passes,
wherein the ligature comprises a tensile load bearing element that reinforces the polymeric body.

2. The composite meniscus implant of claim 1, wherein the top surface, bottom surface, or both, comprise a lubricious coating.

3. The composite meniscus implant of claim 1, wherein the central region of the ligature reinforces the periphery.

4. The composite meniscus implant of claim 1, wherein the anterior end of the ligature is adapted to pass through a first transosseous tunnel and attach to a subject.

5. The composite meniscus implant of claim 1, wherein the posterior end of the ligature is adapted to pass through a second transosseous tunnel and attach to a subject.

6. The composite meniscus implant of claim 1, wherein the tensile load bearing element comprises fiber, yarn, or a combination thereof.

7. The composite meniscus implant of claim 1, wherein the ligature is formed by weft knitting, warp knitting, braiding, weaving, bundling, knotting, looping, and combinations thereof.

8. The composite meniscus implant of claim 1, wherein the ligature, the reinforcing element, or both, are formed by a plurality of fibers.

9. The composite meniscus implant according to claim 1, wherein the ligature and the reinforcing element comprise one or more polymers chosen from polyesters, polyolefins, perhalogenated polyolefins, polyether ether ketones, polyurethanes, polyamides, silicones, nylons, and combinations of two or more thereof.

10. The composite meniscus implant of claim 1, wherein the ligature comprises a mono-filament yarn, a multi-filament yarn, or a combination thereof.

11. The composite meniscus implant of claim 1, wherein each polymeric column in the plurality of polymeric columns has the same width.

12. The composite meniscus implant of claim 1, wherein each polymeric column in the plurality of columns is separated by a distance that is the same between each polymeric column.

* * * * *